United States Patent [19]

Libby et al.

[11] 4,084,136

[45] Apr. 11, 1978

[54] EDDY CURRENT NONDESTRUCTIVE TESTING DEVICE FOR MEASURING VARIABLE CHARACTERISTICS OF A SAMPLE UTILIZING WALSH FUNCTIONS

[75] Inventors: Hugo L. Libby; Bernard P. Hildebrand, both of Richland, Wash.

[73] Assignee: Battelle Memorial Institute, Richland, Wash.

[21] Appl. No.: 734,520

[22] Filed: Oct. 21, 1976

[51] Int. Cl.² ............................................. G01R 33/12
[52] U.S. Cl. ................................................. 324/238
[58] Field of Search .................................... 324/37, 40

[56] References Cited

U.S. PATENT DOCUMENTS

| 3,229,198 | 1/1966 | Libby | 324/40 |
| 3,391,336 | 7/1968 | Hentschel | 324/40 |
| 3,706,029 | 12/1972 | Wandling et al. | 324/40 |
| 3,925,646 | 12/1975 | Richardson et al. | 235/152 |

OTHER PUBLICATIONS

Harmuth, H. F. Transmission of Information by Orthogonal Functions, Springer-Verlag, 2nd Ed., 1972, pp. 30, 31 and 93-95.

Roch et al., Generation of Walsh Function Expansion Coefficients, Proc. of Symp. on Appl. of Walsh Function, 1973, pp. 268-269.

Siemens et al., Walsh Series to Fourier Series Conversion, 1972, Proceeding IEEE, pp. 295-297.

Blachman, N. M.; Sinusoids Versus Walsh Functions, Proc. of IEEE vol. 62, No. 3, Mar. 1974, pp. 346-354.

Primary Examiner—Robert J. Corcoran
Attorney, Agent, or Firm—Klarquist, Sparkman, Campbell, Leigh, Hall & Whinston

[57] ABSTRACT

An eddy current testing device for measuring variable characteristics of a sample generates a signal which varies with variations in such characteristics. A signal expander samples at least a portion of this generated signal and expands the sampled signal on a selected basis of square waves or Walsh functions to produce a plurality of signal components representative of the sampled signal. A network combines these components to provide a display of at least one of the characteristics of the sample.

26 Claims, 24 Drawing Figures

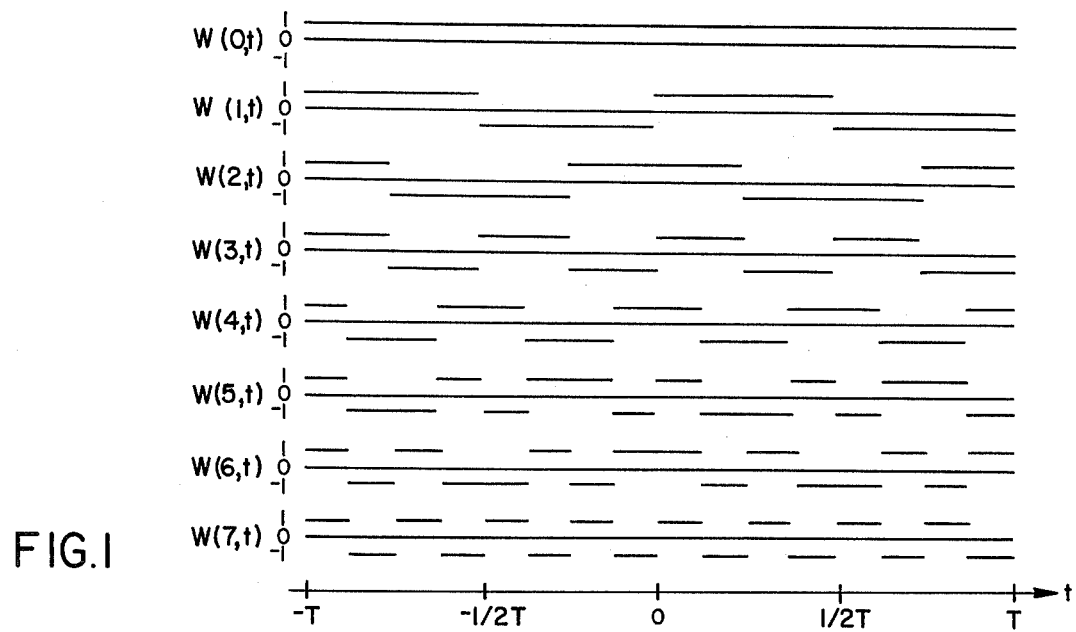
FIG.1
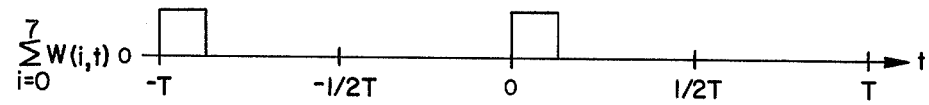
FIG.2
FIG.3
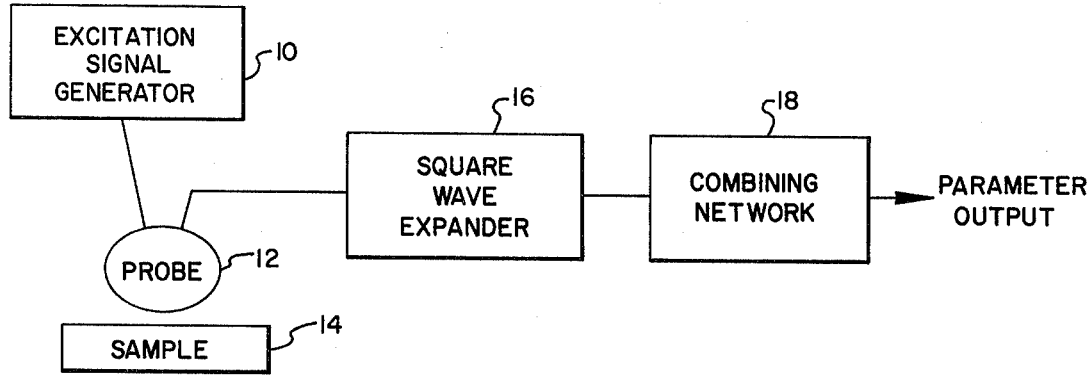
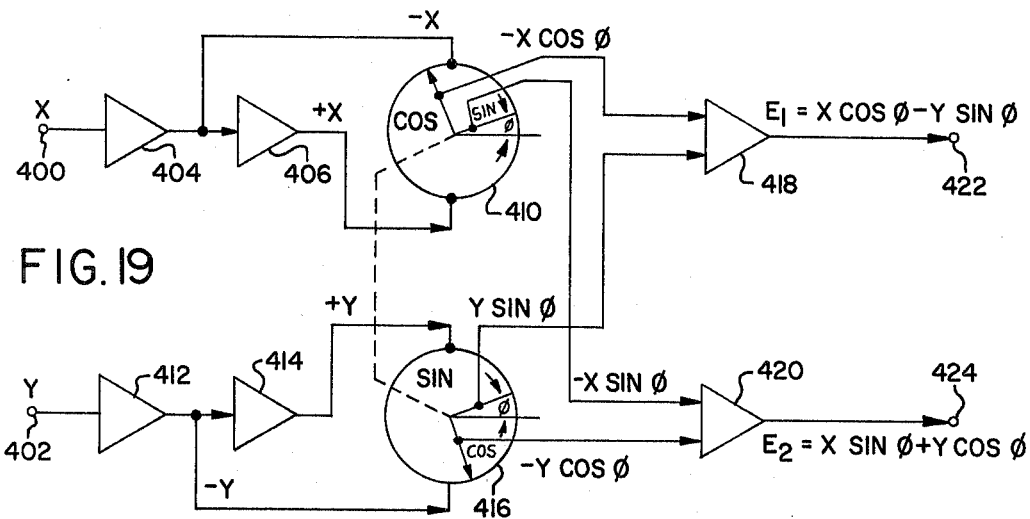
FIG.19

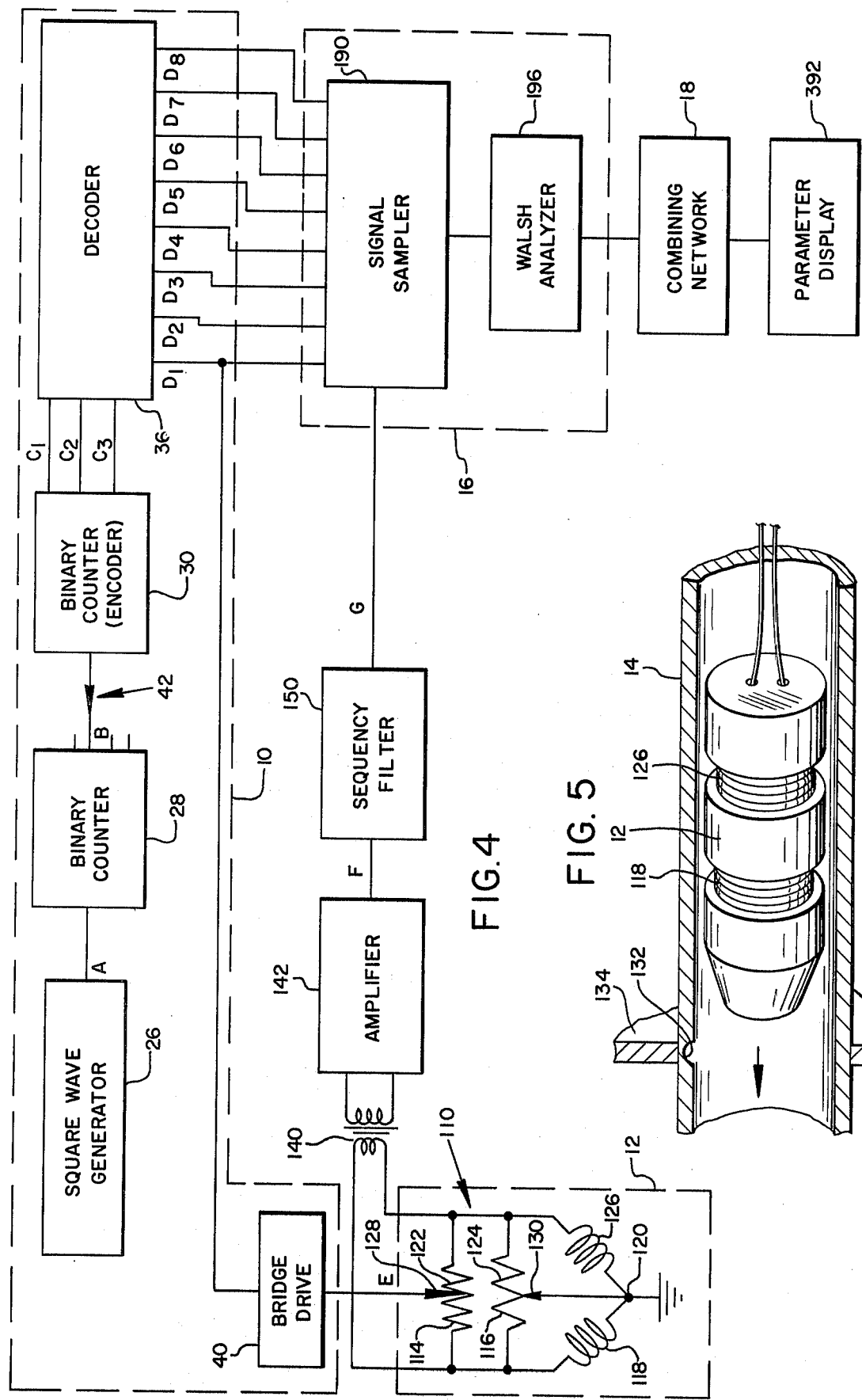

FIG. 14
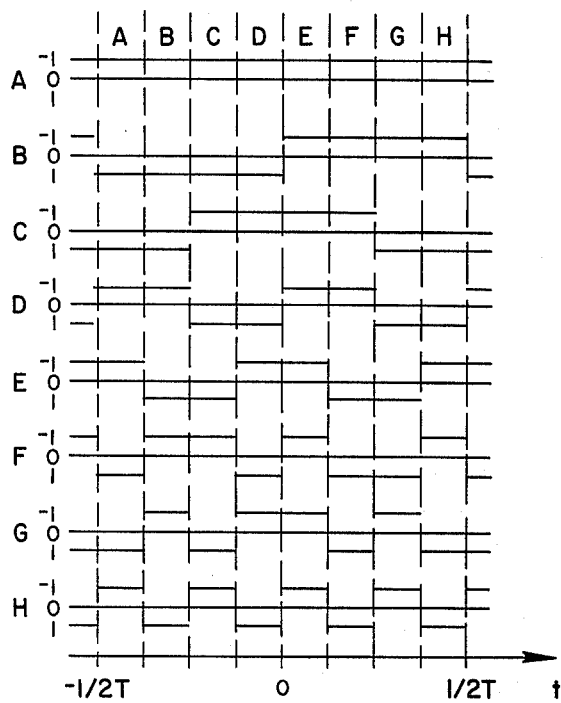
FIG. 14a
FIG. 14b
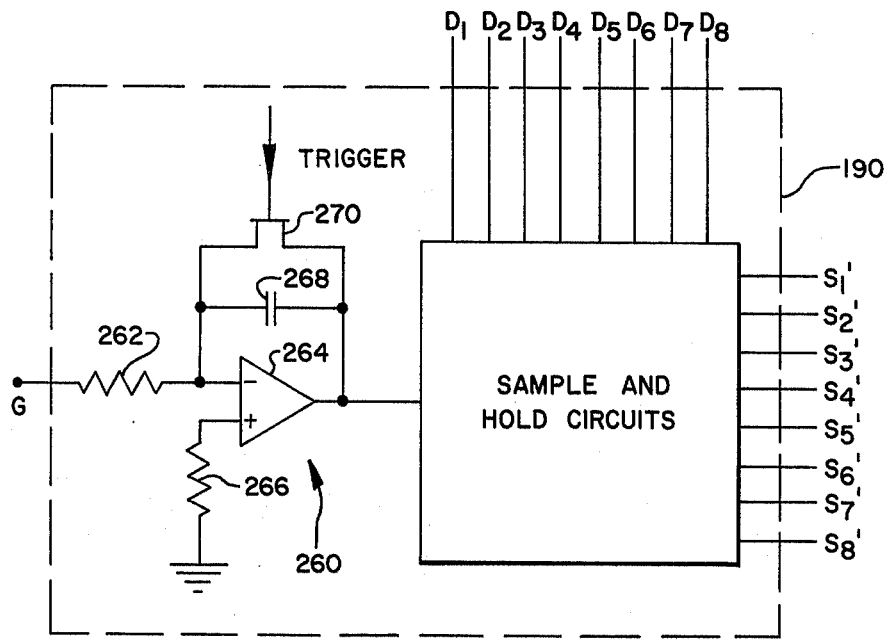
FIG. 15

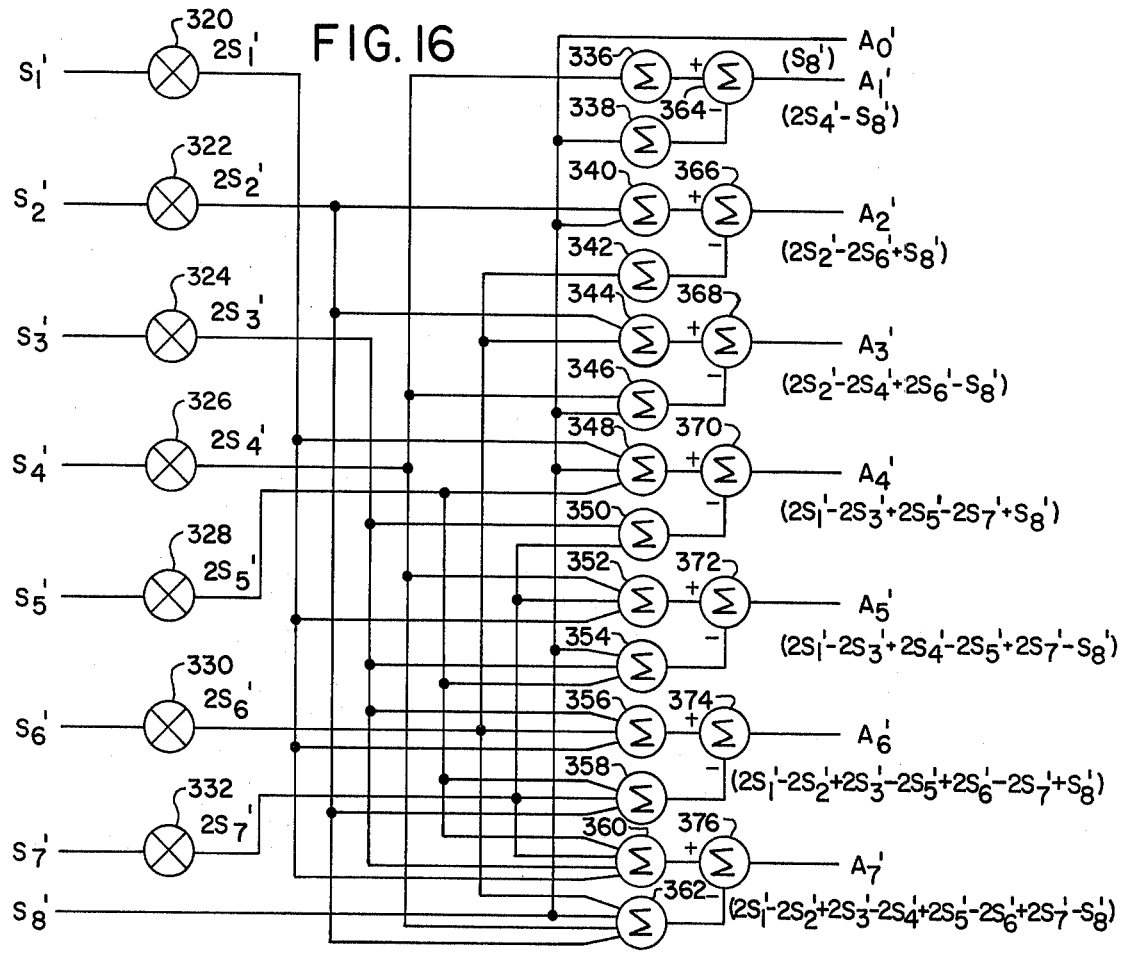
FIG. 16
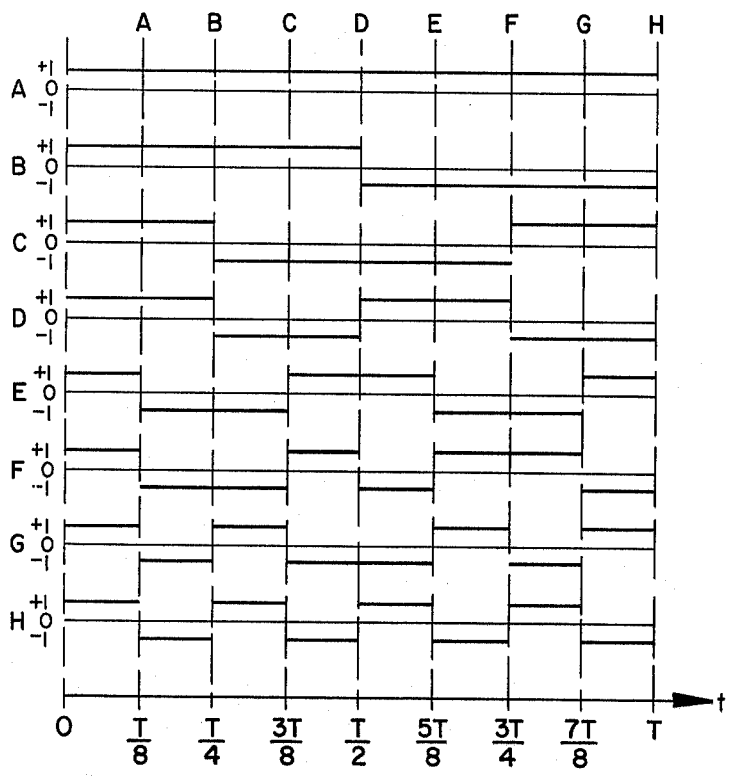
FIG. 17
FIG. 17a
FIG. 17b

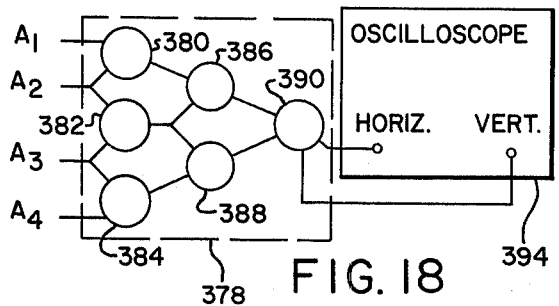
FIG. 18
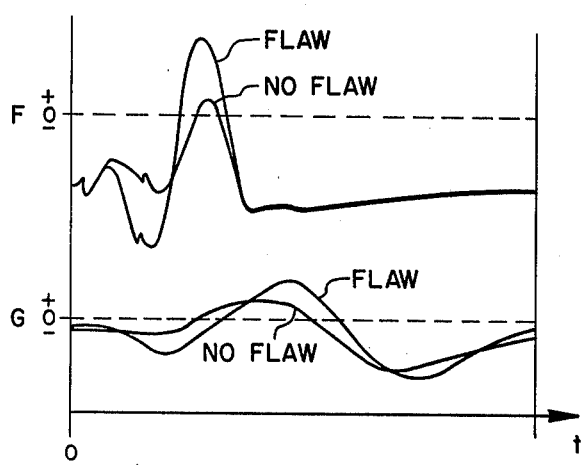
FIG. 22
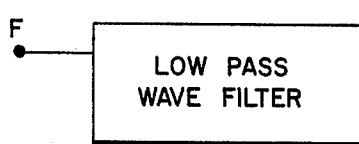
FIG. 21
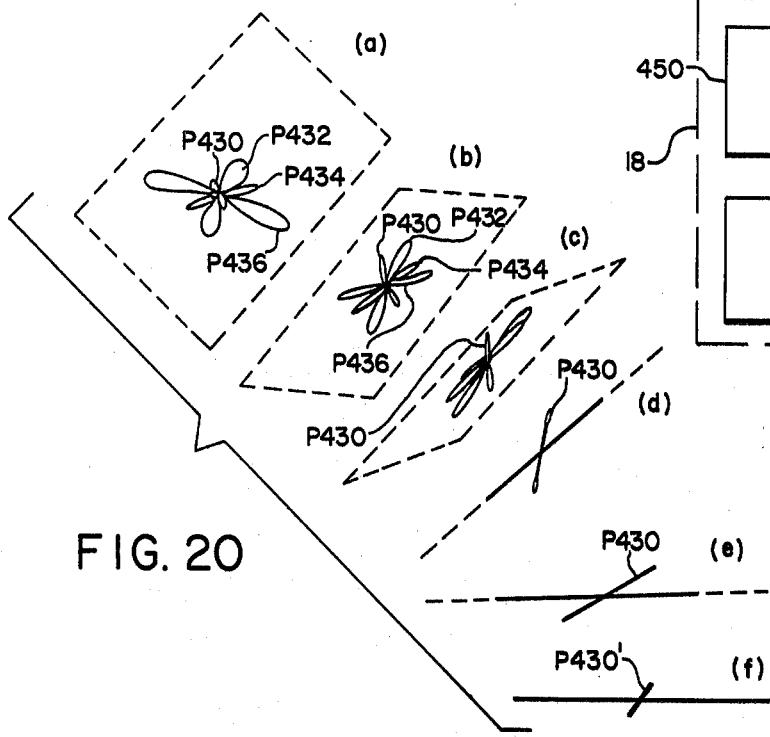
FIG. 20
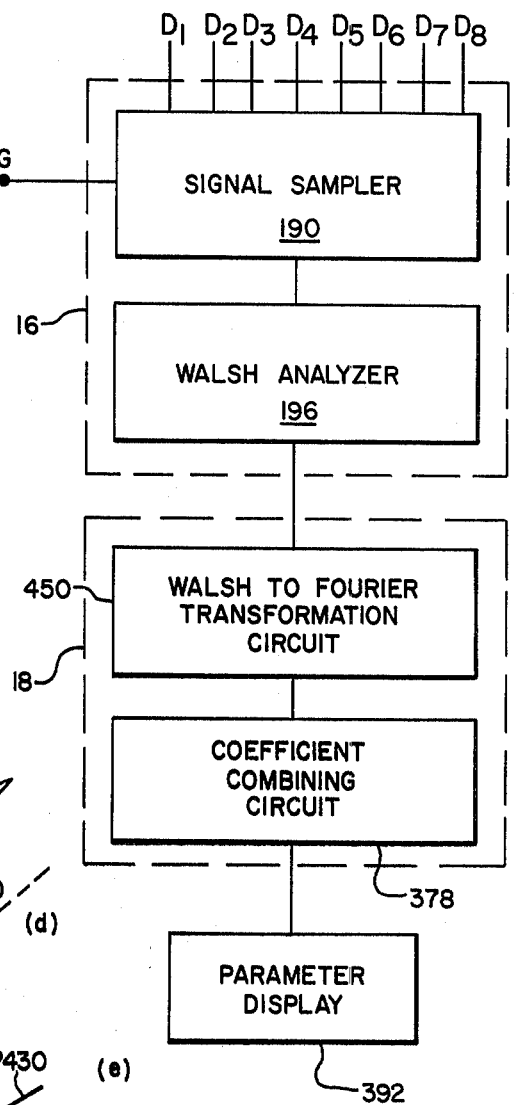

EDDY CURRENT NONDESTRUCTIVE TESTING DEVICE FOR MEASURING VARIABLE CHARACTERISTICS OF A SAMPLE UTILIZING WALSH FUNCTIONS

BACKGROUND OF THE INVENTION

1. Field of the Invention

The present invention relates to nondestructive eddy current testing devices, and more particularly to such devices capable of measuring multiple variable characteristics of a sample.

2. Description of the Prior Art

Conventional nondestructive eddy current testing devices typically utilize a test coil which is placed in proximity to a sample excited by a signal of a single frequency. Single frequency excitation results in an output from the test coil which may be utilized to determine unambiguously the value of two characteristics (i.e. metal plate thickness and electrical conductivity), but not more than two variable characteristics or parameters of the sample. Furthermore, even in applications where additional characteristics of the sample are not of direct interest, their affects on the test coil output may mask characteristics of interest and thereby reduce the effectiveness of the eddy current test. Although in some cases the information obtained from such devices is sufficient, in general, much of the test information concerning the sample remains unrevealed.

To increase the information obtainable from eddy current testing, devices have been developed employing a test coil excited by a multifrequency signal, as exemplified by U.S. Pat. No. 3,229,198 to Libby, or by various single frequency signals applied sequentially, as exemplified by U.S. Pat. No. 3,391,336 to Henschel. These devices typically employ analog computation circuitry and require a measurement of the amplitude and phase of each frequency component of the test coil output in order to resolve the output into a representation of sine and cosine signals.

In the device of Libby, a multidimensional excitation current, described in one embodiment as two superimposed sinusoids, is applied to a test coil. A pair of narrow bandpass filters each receive a portion of the test coil output signal and feed their respective filtered outputs to an amplitude-phase detector circuit. These latter circuits each produce a signal in phase and a signal in quadrature with a fixed reference signal. These four signals, or descriptors, represent the Fourier expansion of the test coil output signal. Hence, the device of Libby expands the test coil output signal on a set of basis functions. Linear potentiometer summing circuits in turn receive these descriptors and are adjusted in a complex one-step manner to eliminate the effects of certain parameters and provide outputs indicative of desired parameters.

The device of the Libby patent, however, is not easily extended to applications in which more than four such descriptors are needed in order to determine the desired information. To obtain a greater number of usable descriptors, the test coil of Libby must be excited by a signal comprised of more than two frequencies. Consequently, more than two narrow bandpass filters will be required for separating the test coil output signal into its respective frequency components, and a corresponding increase in the number of amplitude-phase detection circuits will be required. In addition to the increased complexity, increased cross talk, or coupling, occurs and interferes with the operation of the device.

The problems associated with adjusting the potentiometer summing circuits of the Libby device are somewhat reduced by replacing these circuits with an array of transformation rotators as disclosed in U.S. Pat. No. 3,706,029 to Wandling, et al. However, the arrangement of rotators of Wandling requires a still somewhat complex iterative adjustment of the rotators.

One common drawback of all known eddy current testing devices is their lack of employment of binary functions. This deficiency limits the extent that such devices may utilize digital circuitry and in turn adds to their complexity and cost. Furthermore, for the sake of speed and simplicity in the realm of computers, it is desirable that such devices maximize the extent that they work with binary functions.

It has been discovered that a set of binary functions called Walsh functions may be used as a basis for expansion of an eddy current signal. As a result of this discovery, a relatively simple eddy current testing device has been designed which may be used in a wide variety of eddy current testing applications, including those in which a multiple frequency signal is used for excitation of a test coil.

SUMMARY OF THE INVENTION

The present invention is a nondestructive eddy current testing apparatus or device for measuring one or more variable characteristics of a sample. The device generates a signal which varies in accordance with variations in eddy currents produced in the sample being tested. An expander means expands a received signal corresponding to this generated signal into a plurality of components each proportional to a coefficient of a square wave expansion of the received signal. Advantageously these components are each proportional to a Walsh coefficient of the Walsh series expansion of the received signal. A combining network combines these components to minimize the effects on the received signal caused by certain variables and to produce an output therefrom indicating at least one of the variable characteristics of the sample.

The eddy current testing device of the present invention may take different forms for different applications, but all such forms include a type of expander means for producing a square wave expansion representation of the signal received by the expander means.

More particularly, in one embodiment a probe placed in proximity to a sample receives an excitation signal. This causes the generation of eddy currents in the sample which vary in accordance with the characteristics of the sample and which affect the output of the probe. A signal corresponding to at least a portion of the probe output signal is sampled by a signal sampler means and the samples produced thereby are processed by the expander means into the components proportional to Walsh coefficients. In addition, the output from the combining network is visually displayed.

As a more specific feature, the combining network may include a Fourier transforming means for converting the signals proportional to the Walsh coefficients into signals proportional to Fourier coefficients of the Fourier series expansion representation of the probe output signal. A plurality of these latter components are combined to provide the output from the combining network.

Another feature which the present invention may include is an excitation signal generator means for providing a multifrequency sinusoidal excitation signal, or alternatively, a generator means for providing an excitation signal equivalent to a summation of a finite number of Walsh functions.

Still another feature which may be included is a sequency filter means, a low pass filter means, or combination thereof, for filtering the probe output signal.

A further feature which may be included is a combining network comprising a novel array of transformation rotator units which facilitate the ease of adjusting the combining network to produce the desired output.

It is accordingly one object of the present invention to provide an improved nondestructive eddy current inspection device and method for measuring or testing variable characteristics of a sample.

Another object of the present invention is to provide an improved nondestructive eddy current multiple variable testing device and method.

An additional object of the present invention is to provide an improved nondestructive eddy current multiple parameter testing device utilizing square wave functions, which advantageously take the form of Walsh functions, as a basis upon which a signal produced from eddy currents generated in the sample is expanded.

Still another object of the invention is to provide an improved eddy current testing device which is of simplified design, economical to construct, compact in size, and easily adaptable to digital processing applications.

Another object of the present invention is to provide an improved eddy current testing device which is easy to adjust and operate.

A further object is to provide an improved eddy current testing device which eliminates the need for narrow frequency bandpass filters.

An additional object is to provide an improved eddy current testing device which may be driven by a wide variety of excitation signals.

Still another object is to provide an improved eddy current testing device which increases the number of variable characteristics of the sample which can be identified.

The subject matter which we regard as our invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

BRIEF DESCRIPTION OF THE DRAWINGS

In the drawings:

FIG. 1 is a chart of Walsh functions, ordered by sequency, over the time interval from $-T$ to $+T$;

FIG. 2 is a waveform generated by summing the Walsh functions shown in FIG. 1;

FIG. 3 is a block diagram of a generalized version of a device according to the present invention;

FIG. 4 is a more detailed block diagram of a device according to the present invention;

FIG. 5 is a side elevation view of a probe inserted in a broken away section of a tube;

FIG. 14 is a chart of the Walsh functions of FIG. 1, over the time interval from minus $\frac{1}{2}$ T to $\frac{1}{2}$ T, which have been partitioned into time increments of T/8 duration;

FIG. 14a is an array generated from the chart of FIG. 14;

FIG. 14b is a Hadamard matrix related to the Walsh functions of FIG. 1 which is utilized by the Walsh analyzer of FIG. 13;

FIG. 15 shows an alternative form of signal sampler utilized in the device of FIG. 4;

FIG. 16 is a block diagram illustrating in greater detail an alternative form of Walsh analyzer employed in the device of FIG. 4 when the form of signal sampler of FIG. 15 is utilized;

FIG. 17 is a chart of the Walsh functions of FIG. 1, over the time interval from 0 to T, which have been partitioned into time increments of T/8 duration;

FIG. 17a is an array generated from the chart of FIG. 17;

FIG. 17b is a matrix [Wal'], related to the differentiated Walsh functions of FIG. 17, which is utilized by the Walsh analyzer of FIG. 16;

FIG. 18 is a block diagram of a form of coefficient combining network comprising an array of transformation rotators utilized in the combining network of FIG. 4;

FIG. 19 is detailed block diagram of one form of transformation rotator of FIG. 18;

FIG. 20 is a pictorial representation of planar rotation and transformation using the coefficient combining network of FIG. 18;

FIG. 21 is a block diagram of a portion of a modified device according to the present invention;

FIG. 22 shows two waveforms taken from referenced locations in the device of FIG. 21;

THEORETICAL BACKGROUND AND DEFINITIONS

Figure 6:
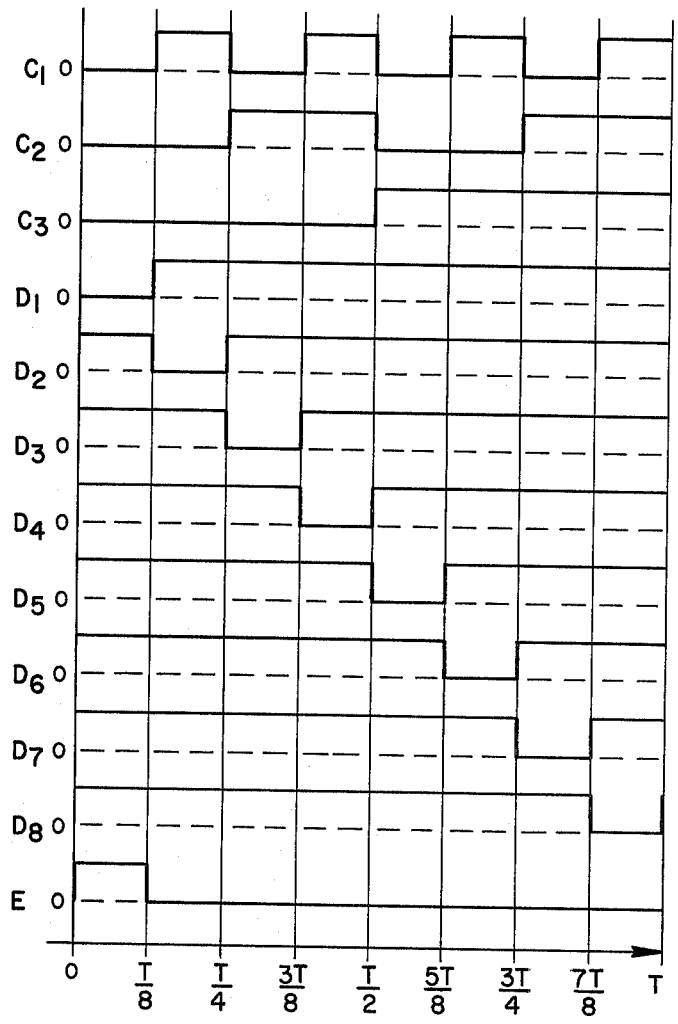
FIG. 6 is a chart of waveforms taken from referenced locations in the device of FIG. 4.

The present invention expands a waveform affected by eddy currents generated in a test sample into a plurality of components representative of the waveform. These components are each proportional to a coefficient of a square wave expansion of the waveform, rather than sine and cosine wave components as in the case of Fourier expansion. This square wave expansion suitably comprises a Walsh function expansion of the waveform.

Walsh functions are complete set of orthonormal functions comprising a series of square waves which take on either the value (+1) or the value (−1) and are of increasing "sequency" or axis crossings. This set of functions may be employed to simulate substantially any arbitrary waveform and therefore can be used as a basis upon which a waveform may be expanded.

The first few Walsh functions as defined herein, having an arbitrary period T, are illustrated in FIG. 1 over the time interval from −T to +T. The Walsh functions may be defined in terms of a series of periodic square waves known as Rademacher functions. These Rademacher functions are designated $R_i(t)$, where $1 \epsilon \{0,1,2,\ldots\}$, have $2^{i-1}$ complete square wave cycles on the unit interval from 0 to T, and alternate between (+1) and (−1). One exception is $R_0(t)$ which is a unit step function (+1) over the whole interval. Although the square wave half-cycles vary in duration from one Rademacher function to another, for a given Rademacher function they are uniform. Thus, Rademacher functions exist wherein a unit step wave is expressed as $R_0$, a single square wave cycle as $R_1$, two cycles as $R_2$, etc. However, unlike Walsh functions, Rademacher functions are an incomplete orthonormal set so that not every waveform can be simulated by a series of Rademacher functions.

The Gray Code is useful in defining the Walsh functions in terms of Rademacher functions. Table A illustrates the conversion of the numbers zero through seven from binary to the Gray Code.

TABLE A

| Decimal number | Binary | Gray Code |
|---|---|---|
| 0 | 000 | 000 |
| 1 | 001 | 001 |
| 2 | 010 | 011 |
| 3 | 011 | 010 |
| 4 | 100 | 110 |
| 5 | 101 | 111 |
| 6 | 110 | 101 |
| 7 | 111 | 100 |

If the binary number is $b_n b_{n-1} b_{n-2} \ldots b_1$ then the Gray Code is $g_n g_{n-1} g_{n-2} \ldots g_1$ and the $g$'s are found from the $b$'s by the following rules:

$g_n = b_n$
$g_{n-1} = b_n \oplus b_{n-1}$
$g_{n-2} = b_{n-1} \oplus b_{n-2}$
$g_1 = b_2 \oplus b_1$ Wherein the symbol $\oplus$ means addition modulo 2.

Now to find a particular Walsh function $W(j,t)$, wherein $j$ is the sequency and $t$ is the independent variable, the three steps below are completed:
1. Write $j$ in binary
2. Convert $j$ in binary to its corresponding Gray Code number
3. Multiply together all Rademacher functions whose subscripts correspond to the position of the 1-bits in the Gray Code number.

The Rademacher functions whose subscripts correspond to the position of the 0-bits in the Gray Code number are omitted. The code word and Rademacher functions line up as shown below:

Gray code . . . $g_4 g_3 g_2 g_1$
Rademacher . . . $R_4 R_3 R_2 R_1$

Thus, if the fourth digit of the Gray Code number (i.e. $g_4$) is a 1, the third digit (i.e. $g_3$) is a 1, the second digit (i.e., $g_2$) is a zero and the first digit (i.e., $g_1$) is a 1, then the particular Walsh function is constructed by multiplying $R_4 \cdot R_3 \cdot R_1$.

Figure 25:
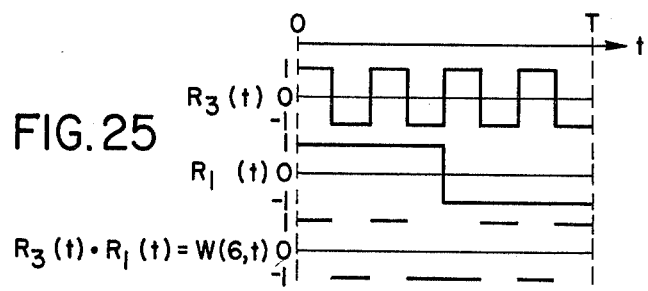
FIG. 25 illustrates the multiplication of the Rademacher functions $R_3$ and $R_1$ to yield the Walsh function $W(6,t)$.

As a specific example, to find $W(6,t)$:
1. 6 = 110 in binary
2. 110 in binary = 101 in Gray code
3. $R_3 \cdot R_1 = W(6,t)$ The above multiplication step 3 is graphically shown in FIG. 25.

In this manner, a complete set of Walsh functions can be obtained from the Rademacher functions.

DETAILED DESCRIPTION OF PREFERRED EMBODIMENTS

With reference to FIG. 3, the eddy current testing device of the present invention includes an excitation signal generator 10 which comprises means for generating and applying an excitation current signal to a probe 12. Positioning the probe 12 in proximity to an electrically conductive sample 14 results in the generation of eddy currents in the sample in response to the excitation signal. The output of the probe 12 is dependent upon these eddy currents and at least a portion thereof is received by an expander means, or square wave expander 16. The expander 16 expands the received signal on a basis of a series of square wave functions. That is, the expander 16 produces a representation of the received signal as a plurality of signal components each one of which is proportional to a coefficient of a square wave expansion of the received signal. Means responsive to these latter components, in this case combining means or network 18, provides at least one parameter output indicative of at least one variable characteristic of the sample 14.

By variable characteristics of the sample or specimen it is meant those characteristics or parameters of the specimen which affect the nature of eddy currents generated in the sample. Examples include such parameters as electrical conductivity, thickness, and the presence and nature of flaws. These parameters are variable in that they may differ from one location in a specimen to another, or between specimens. Differences in these parameters result in an alteration of the eddy currents generated in the specimen and therefore affect and alter the probe output signal. Consequently, the generator 10 and the probe 12 (FIG. 3) may conveniently be considered as a means for generating a signal which varies with variations in the characteristics of the sample.

Other factors, for example wobble or vibration of the probe 12 and the presence of structures supporting the sample, also affect the generated eddy currents and hence the probe output signal. However, their effects, as well as the effects of characteristics of the sample not of interest in the particular application, are discriminated against or minimized by the combining network 18.

It should be noted that in the specification, unless otherwise indicated, the term "square wave" is meant to indicate a periodic wave that alternately assumes one of two relatively fixed values. It is not meant to imply that each square wave half cycle has the same duration, or that there exists a constant ratio between the duration and magnitude of square wave half cycles. Furthermore, the expansion of a signal on a basis of square wave functions, i.e., into a representation of components proportional to coefficients of a square wave expansion of this signal, includes representation by values thereof, e.g., digital values indicative of the magnitude of such square wave components.

EXCITATION SIGNAL GENERATOR

As shown in FIG. 4, the excitation signal generator 10 may comprise a square wave generator means 26, a binary counter means comprising a first binary counter means 28 and a second binary counter means or encoder 30, a decoder means 36 and a bridge drive means 40.

The square wave generator 26 produces an output of uniform square wave pulses and is connected to drive the first binary counter 28. Although the frequency of these pulses may be varied, they may, for example, have a frequency of approximately 7 megahertz.

In response to the input of square wave pulses, first binary counter 28 produces a plurality of binary outputs. Conveniently, each successive adjacent output of counter 28 divides the previous output by two so that its first output will be of a frequency one-half the frequency of the received square wave pulses, its second output will be at half the frequency of its first output, its third output will be at half the frequency of its second output, etc. A switch 42 selectively connects the encoder 30 to one of the outputs of the binary counter 28, such as in FIG. 4 at B. The encoder 30 produces an encoded binary output comprising a series of similarly divided by two binary outputs as shown in FIG. 6 at $C_1$, $C_2$ and $C_3$ wherein the period T in one example is equal to 4.6 microseconds. A Texas Instruments, Inc. synchronous 4 Bit Counter, No. SN74163, may be employed for each the counter 28 and the encoder 30.

The decoder 36 is connected to the encoder 30 and receives the outputs $C_1$, $C_2$ and $C_3$ from the encoder 30. The decoder decodes the encoded binary output to provide a plurality of sampling pulses labeled $D_1$, $D_2$, etc. through $D_8$ (correspondingly labeled in FIG. 6) for purposes explained below. A portion of one of these outputs, in this case $D_1$, is fed to the bridge drive 40 and hence the decoder 36 is coupled to the test coil means or probe 12. The sampling pulses may be constructed from the input waveforms $C_1$, $C_2$ and $C_3$ using the form of decoder 36 illustrated in FIG. 7.

Figure 7:
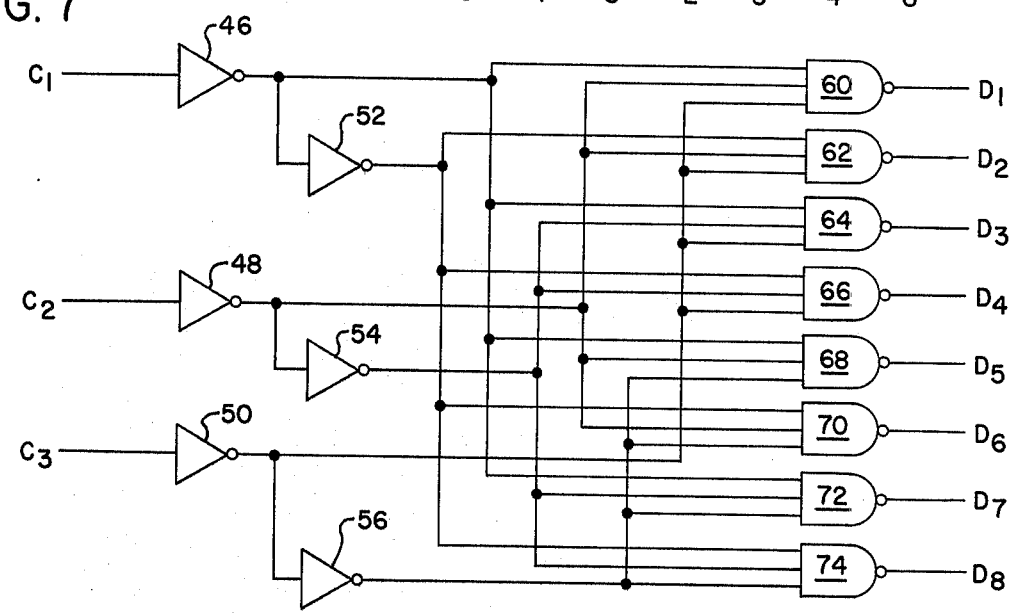
FIG. 7 is a block diagram illustrating the decoder portion of the device of FIG. 4 in greater detail.

The decoder of FIG. 7 comprises a first stage of inverters 46, 48 and 50 which receive and invert the received signals $C_1$, $C_2$ and $C_3$, respectively. A second stage of inverters 52, 54 and 56 receive a portion of the outputs from the inverters 46, 48 and 50, respectively, and re-erect the signals $C_1$, $C_2$ and $C_3$ at their respective outputs. The inverted signal $C_1$ from the inverter 46 is fed to an input of three input nand gates 60, 64, 66 and 72 and the re-erected signal $C_1$ at the output of the inverter 52 is fed to an input of similar nand gates 62, 66, 70 and 74. In a like manner, the inverted signal $C_2$ is fed from the inverter 48 to gates 60, 62, 68 and 70 while the re-erected signal $C_2$ from the inverter 54 is fed to gates 64, 66, 72 and 74. In addition, the inverted signal $C_3$ from the inverter 50 is fed to gates 60, 62, 64 and 66 and the re-erected signal $C_3$ from the inverter 56 is fed to gates 68, 70, 72 and 74.

During the period of time from zero to T/8, the inputs at $C_1$, $C_2$ and $C_3$ are all at a zero logic level (FIG. 6). Consequently, the inputs to gate 60 are all at a logic level of 1. Therefore, the decoder 36 output $D_1$ will be zero during this time interval. On the other hand, the inputs at the respective gates 62 through 74 are not all at a logic level of 1 so that the outputs from these gates during this time interval, as shown in FIG. 6, will be at a logic level of 1. Subsequently, during the interval of time from T/8 through T/4, the input signal $C_1$ becomes positive while the input signals $C_2$ and $C_3$ remain at zero. As a result, only gate 62 will have inputs which are all at a logic level of 1. Therefore, during this time interval, the output from gate 62 will be at a level of zero and the outputs from all the other gates will be a logic 1. The outputs $D_1$, $D_2$, etc. through $D_8$ are produced in this manner.

Conveniently, a Texas Instruments, Inc. 4-line to 10-line monolithic decoder, No. SN7442, may be utilized for decoder 36. It will be apparent that numerous other circuit designs and combinations of logic gates may be readily substituted for the decoder of FIG. 7. Additionally, the decoder 36 and associated circuitry may be readily designed to produce any number of decoder sampling outputs during the time interval from zero through T, and not just eight as described above.

The bridge drive 40 couples the decoder 36 to the probe 12 by receiving and amplifying a portion of the output $D_1$ from the decoder 36 and, responsive to the received signal, applying an excitation current signal to the probe 12. This excitation signal is a periodic square wave having the form shown in FIG. 6 at E. A dual peripheral positive "and" driver, No. SN75450A, produced by Texas Instruments, Inc., or a fast voltage follower buffer amplifier, No. LH0033CG, produced by National Semiconductor, Inc., are two examples of suitable bridge drive circuits.

With reference to FIG. 2, it can be seen that the summation of the first eight Walsh functions comprises a block pulse having a duration of T/8. This waveform is similar in shape, although not of equal magnitude, to the waveform applied by the bridge drive 40. Consequently, the probe excitation current signal has a period T and is a normalized version of, and may be considered equivalent to, the summation of a finite number of Walsh functions. The summation of any finite number of Walsh functions (i.e., the first 4 or 16) may be utilized as the probe excitation signal in place of the illustrated summation of the first eight.

Figure 8:
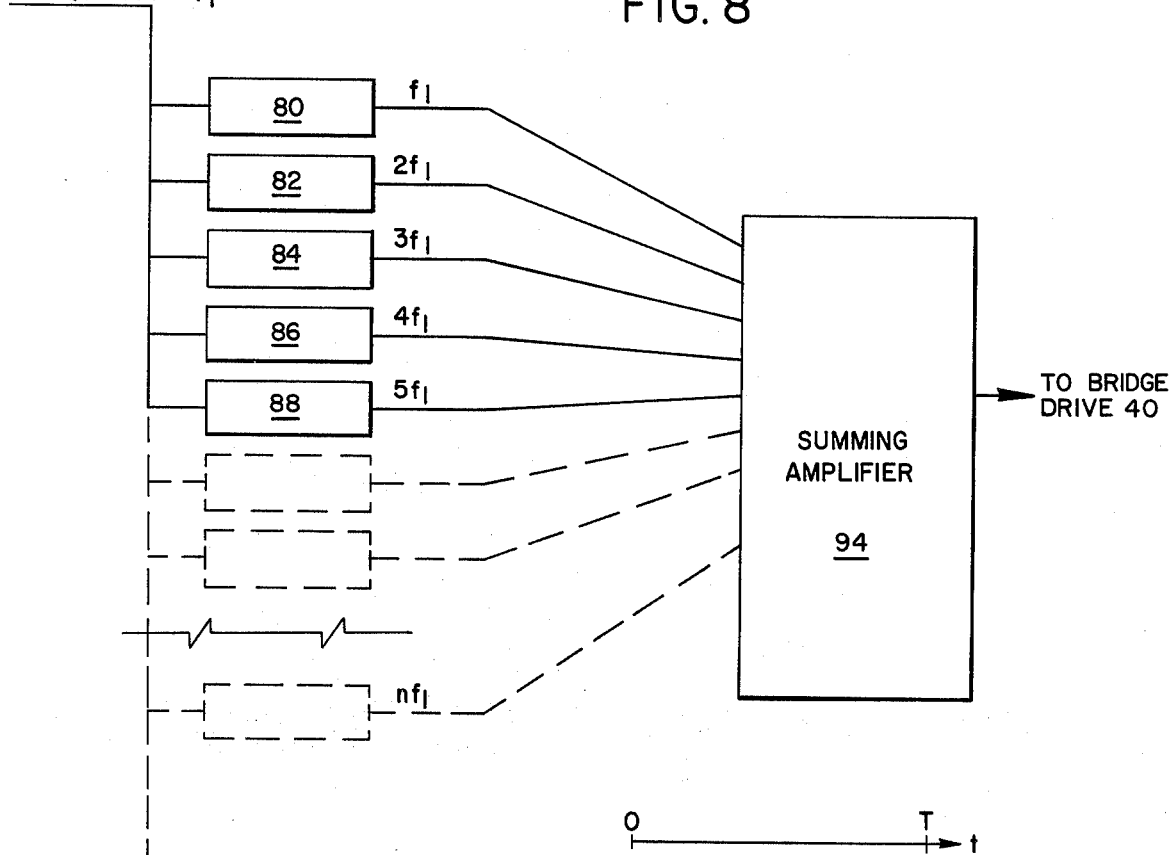
FIG. 8 is a block diagram of a generalized version of a multifrequency sinusoidal excitation signal generator which may be used as an alternative source of excitation in the device of FIG. 4.

In lieu of using a portion of an output from the decoder 36, the probe 12 may be excited by a multifrequency sinusoidal excitation signal produced from a sinusoidal signal generator means, such as shown in FIG. 8. It should be noted that the multifrequency excitation signal also may be periodic over the period T. As illustrated, the sinusoidal generator means comprises a plurality of identical single frequency sine wave function generators 80, 82, 84, 86, 88, etc. and a summing amplifier 94. Each sine wave function generator receives a square wave signal at a frequency $f_1$ from one output of the binary counter 28 and produces a sine wave output of a frequency which differs from one of said generators to another. Any number of such sine wave function generators may be utilized and although the outputs of the generators 80, 82, 84, 86 and 88 are suitably at frequencies $f_1$, $2f_1$, $3f_1$, $4f_1$ and $5f_1$, respectively, these outputs need not be of frequencies integrally related to one another. Means is included, in this case a summing amplifier 94, for summing the outputs from the sine wave function generators to provide a multifrequency sinusoidal excitation signal which is fed to the bridge drive 40 and in turn excites the probe 12.

Figure 9:
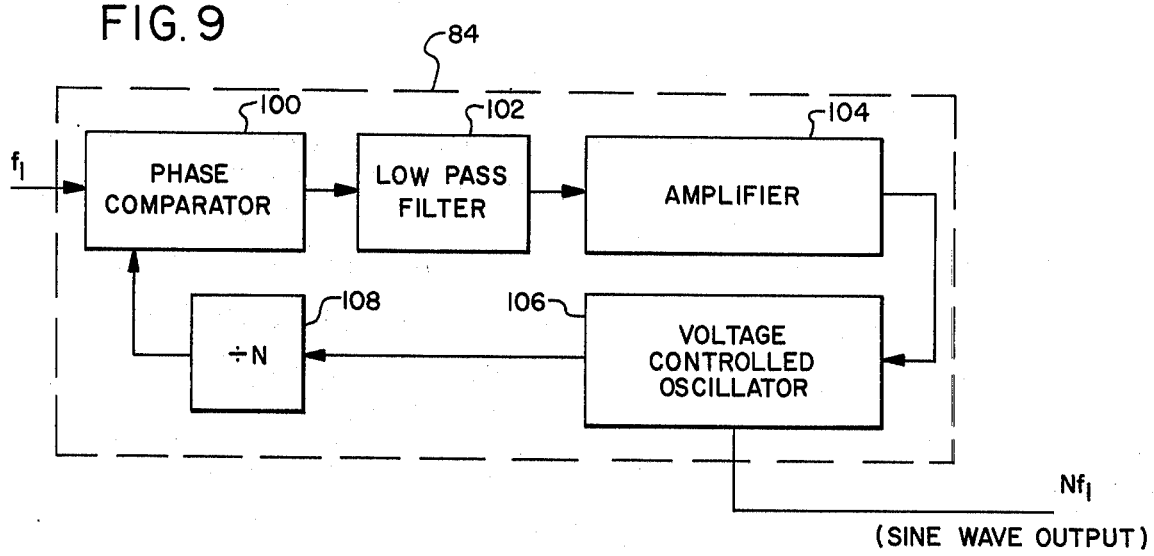
FIG. 9 is a block diagram illustrating one portion of the excitation signal generator of FIG. 8 in further detail.

The sine wave function generators may each be of a phase-lock loop variety as shown in FIG. 9 for generator 84. A phase comparator 100 receives the input signal of frequency $f_1$ and produces an output control signal which is filtered by a low pass filter 102, amplified by an amplifier 104 and fed to a voltage controlled oscillator 106. The oscillator 106 provides a sine wave output having a frequency of $Nf_1$, where N equals three for generator 84. A feedback output from the oscillator 106 is fed to, and divided by, a divide by N frequency divider 108 which in turn is connected to the phase comparator 100. When the inputs to the phase comparator 100 from the binary counter 28 and from the divider 108 are in phase, corresponding to an oscillator output of frequency $Nf_1$, a null control voltage will be produced by the phase comparator 100. A null control voltage causes the frequency of the sine wave output from the oscillator 106 to remain unchanged. However, if the frequency of the sine wave output from the oscillator 106 increases, or decreases, from $Nf_1$, then the inputs to the comparator 100 from the counter 28 and the divider 108 will no longer be in phase. When its inputs are out of phase, the comparator produces a non-null control voltage which operates to return the frequency of the sine wave output of the oscillator 106 to $Nf_1$. Selection of the dividing factor N predetermines the frequency of the sine wave output from the generators 80 through 88, etc. By varying N from one generator to another the sine wave outputs of such generators will be of different frequencies and can be summed by amplifier 94 to produce the multifrequency sinusoidal excitation signal. Driving the sinusoidal frequency generator means of FIG. 8 and also the encoder 30 and the decoder 36 with the counter 28 synchronizes the multifrequency excitation signal with the sampling pulses from the decoder 36. Together, the square wave generator 26, the counters 28, 30 and the decoder 36 constitute one form of synchronization means for synchronizing the sampling pulses and sampler 190 (shown in FIG. 4 and described below) to the excitation signal.

Various forms of probe excitation signals, including single frequency signals, can be used. However, more information concerning the variable characteristics of the sample can be obtained when a broad band excitation signal such as a multifrequency sinusoidal signal, or multifrequency signal equivalent to a summation of Walsh functions, is employed. In general, a particular variable characteristic of the sample will affect each frequency or sequency in an applied broad band signal, although each will be affected by the particular characteristic differently. In addition, the effect on each frequency or sequency due to the different variable characteristics of the sample will generally not be the same. Consequently, when a broad band excitation signal is utilized, the probe output signal, which will also be a broad band signal, can be analyzed in order to obtain a more complete description of the sample than can be obtained by using a single frequency excitation signal.

PROBE

Returning to FIG. 4, although numerous other suitable probe circuits are available, the probe 12 typically comprises a test coil means including an arrangement of one or more test coils such as make up bridge circuit 110. The excitation current from the bridge drive 40 flows through two parallel circuit paths of the bridge circuit 110. The first path includes a resistor 114 connected in series with the parallel combination of a resistor 116 and a test coil 118, which combination in turn is grounded at 120. The second path is similar and includes a resistor 122 in series with the parallel combination of a resistor 124 and a test coil 126 which combination in turn is also grounded at 120. When connected in this manner, the coils 118 and 126 operate differently with the probe or test coil means output signal being the voltage appearing between the non-grounded sides of the two parallel combinations. That is, when the eddy currents in proximity to each of the coils 118 and 126 are substantially identical, a null or minimal probe output signal is produced. On the other hand, a change in the eddy currents in proximity to one of the coils, unaccompanied by similar change in proximity to the other coil, alters the impedance of the circuit containing the former coil relative to the impedance of the circuit containing the other coil to result in a non-null probe output signal. Thus, the coils 118, 126 sense a signal, which may be denoted a first signal caused by eddy currents flowing in the sample 14. Operation at or near a null probe output signal is advantageous because it permits observation of small deviations from nominal variable characteristic values.

The coils 118, 126 are matching and are essentially similar in construction and operation to those of conventional eddy current testing equipment. However, they must be operable over a broad range of excitation signal frequencies. Due to unavoidable differences in the assembly of the coils and in their construction, as well as to the existence of stray coupling, it is difficult to obtain a null probe output signal with only the coils 118 and 126. Therefore, the relative magnitude of the resistors 114, 116, 112 and 124 may be adjusted to balance the output from the probe 12 to a null level. More particularly, moving the position of a wiper arm 128 changes the relative magnitude of resistors 114 and 122. In addition, altering the position of a wiper arm 130 changes the relative magnitude of resistors 116 and 124. The wiper arms 128, 130 may be adjusted to produce a null probe output signal whenever the coils 118, 126 sense substantially identical eddy current signals in the sample 14.

FIG. 5 illustrates a suitable probe 12 inserted in a cylindrical tube or sample 14. When in the position shown, the coils 118 and 126 are adjacent to uniform sections of the tube. Consequently, the eddy currents generated in the tube adjacent to each of the coils will be essentially the same and result in a null probe output signal. Thereafter, as the probe is moved in the direction of the arrow in FIG. 5, the coil 118 approaches a defect or notch 132 in the tube, located in this instance underneath a support structure 134. At the time the coil 118 is positioned in proximity to the defect, the coil 126 is still adjacent to a flawless region of the tube. The flaw causes the eddy currents in the tube adjacent to the coil 118 to vary from those flowing in proximity to the coil 126. This in turn unbalances the bridge 110 to produce a non-null probe output signal. In this manner, the output signal from the test coil means or the probe 12 varies in accordance with the variable characteristics of the sample 14.

The output from the probe 12 is fed through an isolation transformer 140 and is amplified by a conventional single ended broad band amplifier 142 having low noise and low distortion. The output signal from the amplifier 142 thus corresponds to the output signal of the test coil means or probe 12.

FILTERING MEANS

Although not required, a filtering means, such as a sequency filter 150 (FIG. 4), may receive and filter the output signal from the amplifier 142. When the filtering means is included, the output from the filtering means corresponds to, and may be defined as a portion of, the probe output signal.

Figure 10:
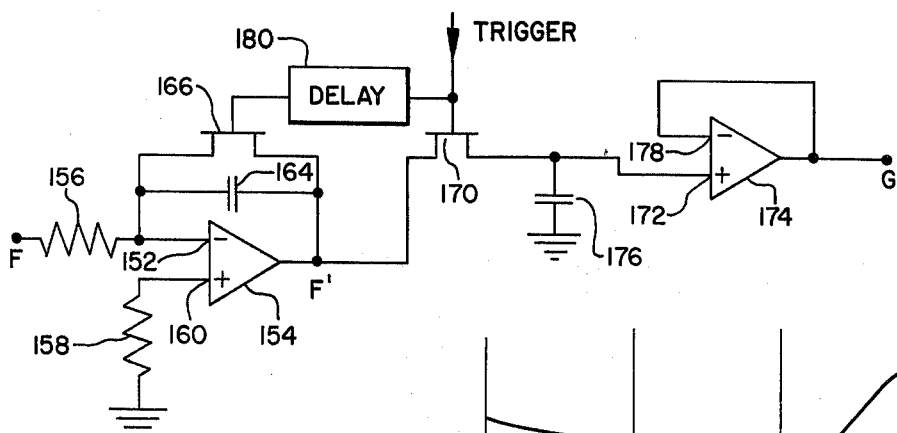
FIG. 10 is a more detailed block diagram of a sequency filter employed in the device of FIG. 4.
Figure 11:
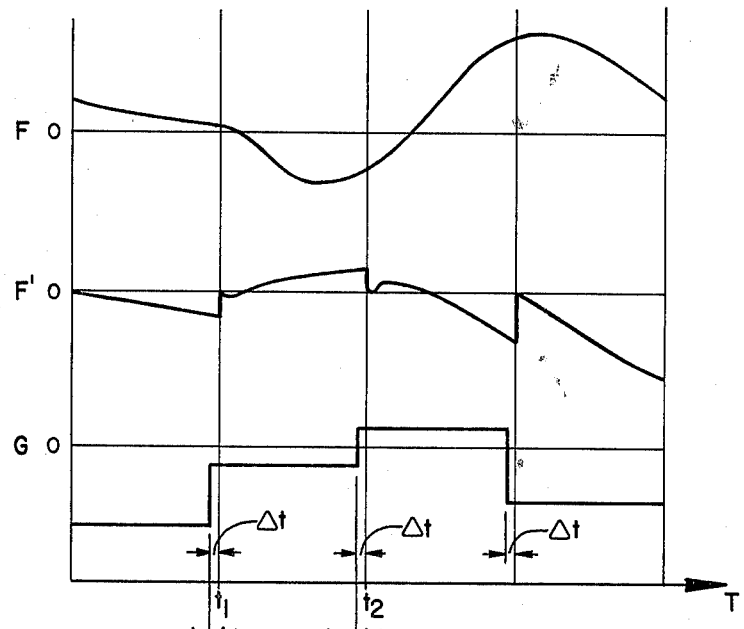
FIG. 11 is a chart of waveforms taken from referenced locations in the sequency filter of FIG. 10.

More specifically, with reference to FIGS. 10 and 11, the sequency filter 150 squares up the shape of the signal received at its input F from the amplifier 142 and enables the square wave expander (FIG. 3) to more easily utilize the probe output signal. The inverting input 152 (FIG. 10) of a first operational amplifier 154 is connected by a resistor 156 to the amplifier 142. A second resistor 158 is connected between the non-inverting input 160 of the operational amplifier 154 and ground. An integrating capacitor 164 is connected between the input 152 and the output F' of the operational amplifier 154. In addition, a switch 166 is connected in parallel with the capacitor 164. The switch 166 may comprise a MOSFET switch and is operable in response to a gating voltage or control signal alternately to open, permitting the integration of the signal from the amplifier 142 by the capacitor 164, and to close, permitting the capacitor 164 to discharge therethrough. A switch 170 connects the output from the op-amp 154 to the non-inverting input 172 of a second operational amplifier 174. A holding capacitor 176 is connected between the input 172 and ground and the inverting input 178 of the op-amp 174 is connected directly to the output G of the op-amp 174. The switch 170 may also comprise a MOSFET and is operable in response to a control or gating voltage to periodically close to enable, at times when the switch 170 is closed, the voltage across the capacitor 164 to appear across the capacitor 176.

The operation of the sequency filter 150 will be described with reference to FIG. 11 wherein FIG. 11 shows at F a typical signal fed from the amplifier 142 to the input F. During the time interval from zero to $t_1$, the switch 166 is open and the capacitor 182 integrates the signal received at input F. The inverted form of this integrated signal (see FIG. 11 at F') appears at the output F' of the op-amp 154. At a time $t_1$-$\Delta t$, a control signal triggers the normally open switch 170 causing it to momentarily close for a time $\Delta t$. When the switch 170 is closed, the voltage across the capacitor 176 tracks the input input signal at F' and holds the instantaneous value attained when the switch 170 reopens. The voltage impressed upon the capacitor 176 will remain unchanged until time $t_2$-$\Delta t$ and other such times that the switch 170 again closes. This occurs because, when the switch is open, the capacitor 176 is isolated from any load through the op-amp 174. The output at G of the sequency filter 150, shown in FIG. 11 at G, corresponds to the voltage across the capacitor 176 and comprises a squared up version of the waveform received at its input F. At time $t_1$, and subsequent times $t_2$, etc., the switch 166 momentarily closes, in response to a control signal received from a conventional delay circuit 180, so that the capacitor 164 discharges through the switch 166 and reduces the signal at F' to zero. The delay circuit 180 receives a portion of the switch 170 control signal and delays this input a time increment $\Delta t$ to provide the control signal for the switch 166. The delay $\Delta t$ is very small, being just long enough to allow the voltage at F' to appear across the capacitor 176.

It should be noted that the switch 166 must be closed for a limited period of time in order for the capacitor 164 to discharge completely and return the voltage at F' to zero. Thus, when the switch 166 is closed, the signal from the amplifier 142 would normally be lost. However, such a loss may be avoided by using two alternately operating sequency filters of the form of FIG. 10. When one such sequency filter is being reset, the other receives the signal from the amplifier 142, and vice versa.

In general, the time periods zero to $t_1$, $t_1$ to $t_2$, etc., are identical. However, the duration of such periods may be varied so that they are no longer than the period of the highest frequency eddy current signal of interest.

SIGNAL SAMPLER

The type of square wave expander 16 illustrated in FIG. 4 includes a signal sampling means or signal sampler 190 for providing samples of the signal it receives. This received signal, whether filtered or not, may be denoted a second signal and corresponds to at least a portion of the output signal or waveform generated by the probe 12. In addition, the expander 16 of FIG. 4 also includes means for combining the sampled values to produce a representation of the generated signal as a plurality of signals each proportional to a coefficient of a square wave expansion of the generated signal. This means may comprise a Walsh expander means for combining the sample produced by the signal sampler 190 into a series of Walsh function representations of the generated signal. Furthermore, when this means takes the form of the illustrated Walsh analyzer means 196 (FIG. 4), such representations comprise a plurality of signals each proportional to a Walsh coefficient of a Walsh wave expansion of the signal. It should be noted that the signal sampler 190 may be considered as a part of, or alternately separate from, the Walsh expander means or analyzer 196.

Figure 12:
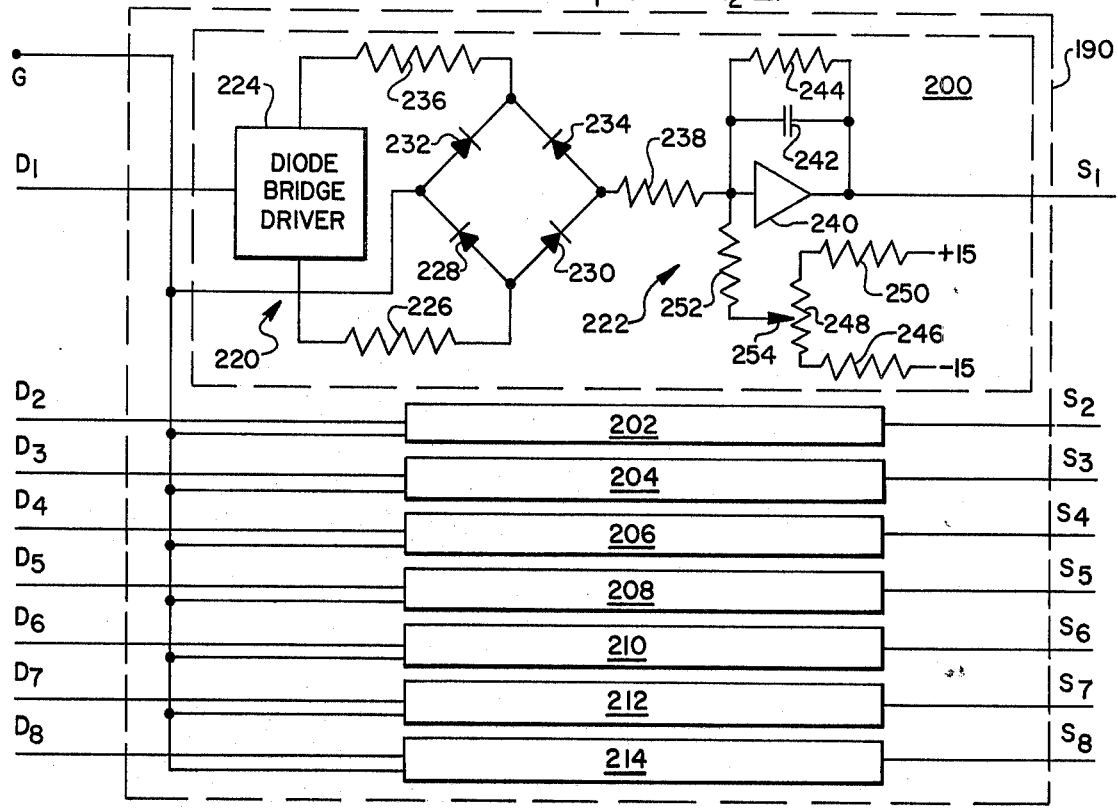
FIG. 12 is a block diagram of one form of signal sampler utilized in the device of FIG. 4.

One type of suitable signal sampler 190 is shown in FIG. 12 and comprises eight identical sample and average circuit means 200, 202, 204, 206, 208, 210, 212 and 214. These sample and average circuits are coupled to the decoder 36 to receive at one input a respective one of the sampling pulses $D_1$ through $D_8$ (FIG. 6) from the decoder 36, and at another input the output from the sequency filter 150. Each sample and average circuit, operating in response to its received sampling pulse, integrates the output signal produced by the sequency filter 150 during the time of its received sampling pulse to produce one stored sample of the sequency filter output signal during each period T. Furthermore, the sample and average circuits 200 through 214 together produce a plurality of such samples, designated $S_1$ through $S_8$ in FIG. 12, respectively. Thus, the sample and average circuit means periodically sample and average the signal received by the sampler 190 over consecutive periods of time, in this case each consecutive period having a duration T/8, during each period T.

Since the sample and average circuits are identical, only the sample and average circuit 200 will be described in detail. The sample and average circuit 200 comprises a bridge portion 220 and an integrator or average portion 222. The bridge portion 220 includes a conventional diode bridge driver 224 which receives at its input the sampling pulse $D_1$. A resistor 226 is connected between the bridge driver 224 and the connected anodes of two diodes 228, 230. The cathode of the diode 228 is connected to the anode of a diode 232. The cathode of the diode 230 is connected to the anode of a diode 234 and also to the input of integrator portion 222. The diodes 232 and 234 are connected together at their anodes and a resistor 236 is connected between these anodes and the diode bridge driver 224. The diodes 228, 230, 232 and 234 thus comprise a four-diode bridge. In addition, the output at G from the sequency filter 150 is connected to the anode of the diode 232.

The integrator portion 222 includes a resistor 238 connected between the cathode of the diode 230 and an operational amplifier 240. An integrating or averaging circuit comprising a capacitor 242 connected in parallel with a resistor 244 is connected between the input and the output of the op-amp 240. In addition, an offset voltage balancing circuit is provided which comprises the resistors 246, 248 and 250 connected in series between DC voltage sources of +15 and −15 volts, a resistor 252 connected between the input of the op-amp 240 and a wiper arm 254 which in turn is connected to resistor 248. Adjustment of the wiper arm 254 adjusts the DC voltage at the input of the op-amp 240 to reduce the DC output voltage to zero.

When the bridge driver 224 receives the sampling pulse $D_1$ it drives all of the diodes into conduction for the duration of the pulse $D_1$. This in turn causes the voltage appearing at the anode of the diode 232, that is, the analog output signal from the sequency filter 150 occurring during the duration of the sampling pulse, to appear at the cathode of the diode 230. The averaged value of the sampled signal appears across the capacitor 242. When the next (and subsequent) sampling pulse $D_1$ occurs, the voltage across the capacitor 242 rises or falls towards a new average value and the process is repeated.

An alternative form of signal sampler 190 which may be used is shown in FIG. 15. Unlike the sampler 190 of FIG. 12, an integrator means or circuit 260 is provided to integrate the output signal from the sequency filter 150 over successive periods of time T. Furthermore, sample and average circuit means sample the integrated output signal from the integrator circuit 260 to produce separately stored samples (Labeled $S_1'$ through $S_8'$ in FIG. 15 to distinguish them from the samples $S_1$ through $S_8$ produced by the sampler 190 of FIG. 12.) corresponding to the output of the sequency filter 150. The sample and average circuit means may be identical to that described above in connection with FIG. 12 and consequently will not be described in detail.

The integrator circuit 260 comprises a resistor 262 connected between the output of the sequency filter 150 and the inverting input of an operational amplifier 264. The non-inverting input of the op-amp 264 is grounded through a resistor 266. An integrating capacitor 268 is connected between the input and output of the op-amp 264 and a switch 270, typically a MOSFET switch, is connected in parallel with this capacitor. The capacitor 268 integrates the signal from the sequency filter 150 over successive periods of time T (i.e., zero to T, T to 2T, etc.). At the end of such period T, the switch 270 momentarily closes in response to a triggering or control signal and enables the capacitor 268 to discharge or dump through the switch 270 and reduce the voltage at the output of the op-amp 264 to zero. Therefore, during each interval of time T, the analog signal from the sequency filter 150 is continuously integrated and this integrated signal is periodically sampled by sampler 190 to provide the plurality of separately stored samples $S_1'$ through $S_8'$.

Thus, during each interval of time T, the samplers 190 of FIGS. 12 and 15 provide a plurality of separately stored samples which together constitute an array of values, with each value representing the sample provided by one sample and average circuit. Sampling, integration and averaging of these values are repeated on a cyclical basis to produce successive arrays of values during successive intervals of time on a real time basis.

Although the illustrated samplers 190 produce and store eight samples per cycle, it will be understood that this number is by way of example only and that these circuits may readily be altered to produce a greater or lesser number of samples per cycle depending on the accuracy desired.

WALSH ANALYZER

The Walsh analyzer 196 comprises a means for combining the values or samples produced by the signal sampler 190 to provide an expansion representation of the signal received from the filtering means, (i.e., the sequency filter 150) on the basis of a series expansion of Walsh waves. More particularly, when the values making up the array for each period T have been stored in the sampler 190, the analyzer 196 transforms these samples into an array of a plurality of values representing the amplitude coefficients of the various Walsh functions of the Walsh series into which the received signal input to the sampler 190 may be spectrally decomposed. Thus, the Walsh analyzer 196 comprises means for changing or spectrally decomposing the input signal thereto into a series expansion of Walsh function representations which may comprise signals proportional to the coefficients of a set of Walsh functions. The size of the Walsh analyzer varies depending upon the number of coefficients to be resolved.

Figure 13:
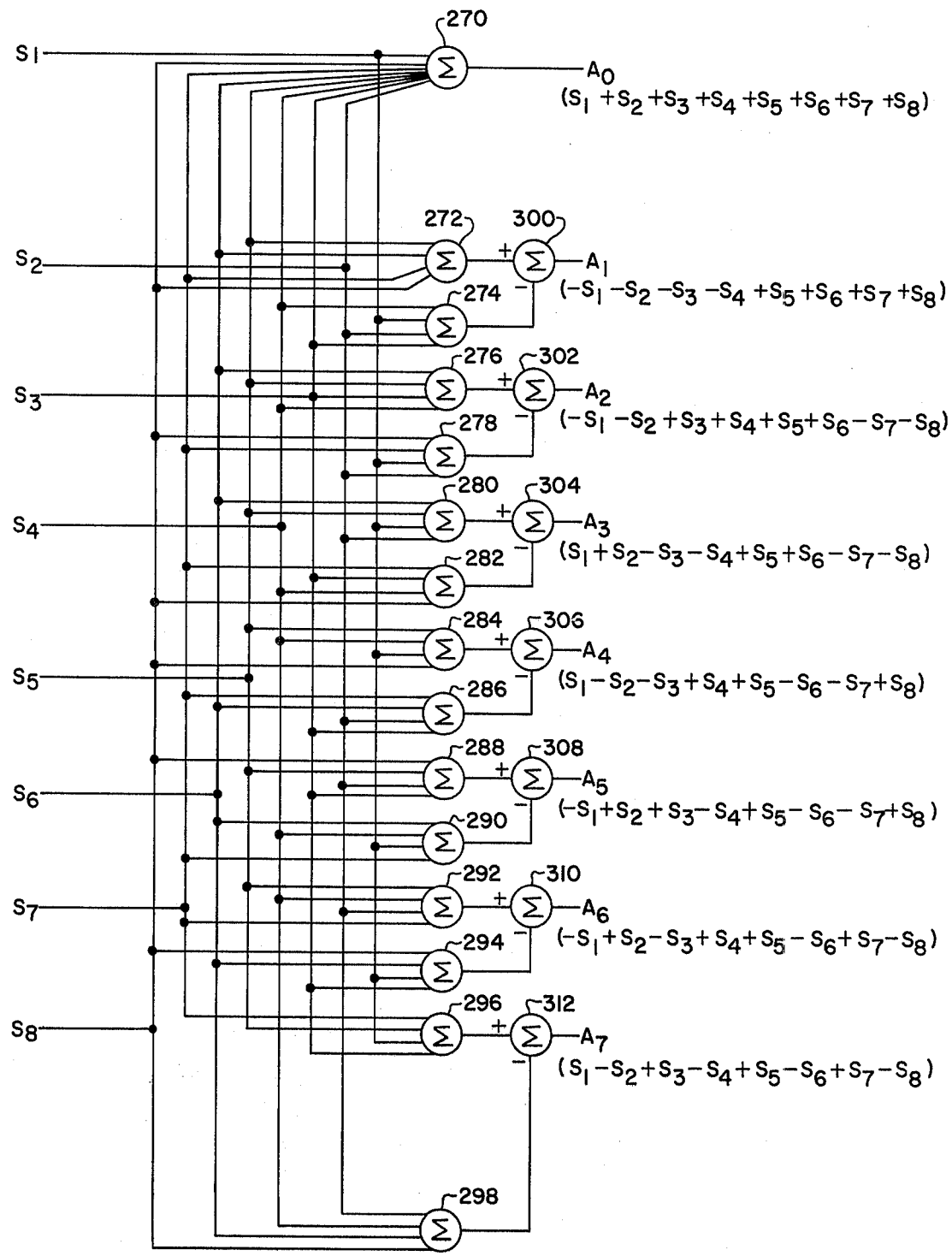
FIG. 13 is a block diagram illustrating in greater detail a form of Walsh analyzer employed in the device of FIG. 4 when the form of signal sampler of FIG. 12 is utilized.

The Walsh analyzer shown in FIG. 13 may be employed when the sampler 190 of FIG. 12 is utilized. This analyzer comprises a first level of summation circuits 270 through 298 which are each capable of carrying out addition and a second level of summation circuits 300 through 312 capable of carrying out addition and subtraction. In the first level, various combinations of the samples $S_1$ through $S_8$ from the similarly labeled outputs of the sampler 190 (FIG. 12) are computed. With the exception of the output of summation circuits 270, these partial results are coupled to the second level where the indicated sums and differences are formed. The output signal $A_0$, from the summation circuit 270, and output signals $A_1$ through $A_7$, one from each one of the summation circuits of the second level, are each proportional to a Walsh coefficient of the Walsh series expansion of the signal received by the sampler 190. Thus, the coefficient for Walsh function $W(0,t)$, i.e., $A_0$, equals $(S_1 + S_2 + S_3 + S_4 + S_5 + S_6 + S_7 + S_8)$, the coefficient for the Walsh function $W(1,t)$, i.e., $A_1$, equals $(-S_1 - S_2 - S_3 - S_4 + S_5 + S_6 + S_7 + S_8)$, for $W(2,t)$, i.e., $A_2$, equals $(-S_1 - S_2 + S_3 + S_4 + S_5 + S_6 - S_7 - S_8)$, for $W(3,t)$, i.e., $A_3$, equals $(S_1 + S_2 - S_3 - S_4 + S_5 + S_6 - S_7 - S_8)$, for $W(4,t)$, i.e., $A_4$, equals $(S_1 - S_2 - S_3 + S_4 + S_5 - S_6 - S_7 + S_8)$, for $W(5,t)$, i.e., $A_5$, equals $(-S_1 + S_2 + S_3 - S_4 + S_5 - S_6 - S_7 + S_8)$, for $W(6,t)$, i.e., $A_6$, equals $(-S_1 + S_2 - S_3 + S_4 + S_5 - S_6 + S_7 - S_8)$ and for $W(7,t)$, i.e., $A_7$, equals $(S_1 - S_2 + S_3 - S_4 + S_5 - S_6 + S_7 - S_8)$.

The analyzer of FIG. 13 forms combinations of the samples from the sampler 190 (FIG. 12) which combinations are determined in accordance with certain Hadamard matrices of order $2^n$ (where $n \in \{0,1,2,...\}$) as explained below. A Hadamard matrix is an orthogonal matrix with elements +1 and −1 only. Consequently, the Walsh analyzer 196 comprises a means for multiplying a matrix [H] and column matrix [S] of the stored samples, in this case $S_1$ through $S_8$, for the solution of the equation [A] = [H] [S]. In this equation, the matrix [A] constitutes a column matrix of the desired signals proportional to the Walsh coefficients (i.e., $A_0$ through $A_7$) and the matrix [H] is a Hadamard matrix related to the Walsh functions for producing Walsh coefficients from the samples.

The generation of the related Hadamard matrix for converting a group of eight samples into the eight signals proportional to the Walsh coefficients will be described with reference to FIG. 14. The Walsh waves of FIG. 1 are illustrated in FIG. 14 over the interval of time from minus $\frac{1}{2}T$ to $\frac{1}{2}T$ and are labeled A through H, with A corresponding to $W(0,t)$, B corresponding to $W(1,t)$, etc. Therefore, the rows A through H correspond to an array of Walsh functions ordered by sequency from $W(0,t)$ through $W(7,t)$. Eight equal sub-increments of time are formed over the interval $-\frac{1}{2}T$ to $\frac{1}{2}T$ and result in columns A through H comprised of the Walsh waves during the sub-increments corresponding to each column. Thus, A is a column of the Walsh waves $W(0,t)$ through $W(7,t)$ over the time increment from minus $\frac{1}{2}T$ to minus $\frac{3}{8}T$, B is a column of the Walsh waves over the time increment from minus $\frac{3}{8}T$ to minus $\frac{1}{4}T$, etc.

The array of FIG. 14a is constructed from the similar rows and columns of the subdivided chart of Walsh functions of FIG. 14 and hence corresponding rows and columns of these figures are similarly labeled. During the time increment represented by column A (FIG. 14), the waveform of row A is positive. For this reason, row A, column A (FIG. 14a) is assigned a plus. During the time increment of column B (FIG. 14), the waveform of row A is also positive. Consequently, row A, column B (FIG. 14a) is also assigned a plus. In this manner, by assigning a plus to an element in a particular row and column of the array of FIG. 14a when the waveform of the corresponding row and column of FIG. 14 is positive, and a minus when the waveform of the corresponding row and column of FIG. 14 is negative, the array of FIG. 14a is formed.

The Hadamard matrix of rank 8, shown in FIG. 14b, is constructed from the array of FIG. 14a. A value of plus one is assigned to elements located in rows and columns of the FIG. 14b matrix when the elements in the corresponding rows and columns of the FIG. 14a array contain a plus and a value of minus one is assigned when the corresponding elements in the array of FIG. 14a contain a minus. The analyzer of FIG. 13 multiplies the FIG. 14b Hadamard matrix by the column of samples $S_1$ through $S_8$ to produce the signals $A_0$ through $A_7$. The Hadamard matrix of FIG. 14b is related in this manner to the Walsh functions for producing eight signals proportional to the Walsh coefficients from the group of eight samples. In a similar manner, the Hadamard matrices of rank 4, 16, etc. can be generated for applications wherein a lesser or greater number of signals proportional to Walsh function coefficient outputs are to be obtained from a lesser or greater number of samples.

When the type of sampler 190 illustrated in FIG. 15 is utilized, the Walsh analyzer 196 takes a somewhat different form from that described above. This alternative form, shown in FIG. 16, is based on the real time integration method described by Koch and Paul in the article entitled, "Generation of Walsh Function Expansion Coefficients," in Applications of Walsh Functions, 1973 Proceedings of the 4th Symposium, pp. 268-269. This form of the Walsh analyzer 196 comprises a group of multipliers 320 through 332 which respectively receive one of the samples $S_1'$ through $S_7'$ and multiply the received sample by two. The multiplied values $S_1'$ through $S_7'$, together with the unmultiplied signal $S_8'$, are fed in various combinations to a first level of summation circuits 336 through 362 each of which is capable of carrying out addition. A second level of summation circuits 364 through 376, each capable of carrying out addition and subtraction, receive the partial results from the first level of circuits 336 through 362 to produce the indicated sums and differences. The output signal $A_0'$ and single output signal from each one of the summation circuits of the second level, $A_1'$ through $A_7'$, respectively, are each proportional to a Walsh coefficient of the Walsh series expansion of the signal received by the sampler 190 (FIG. 15). These outputs are designated $A_0'$ through $A_7'$ to distinguish them from the coefficient outputs $A_0$ through $A_7$ from the analyzer of FIG. 13. Thus, the coefficient for the Walsh function $W(0,t)$, i.e., $A_0'$, equals $(S_8')$, for $W(1,t)$, i.e., $A_1'$, equals $(2S_4' - S_8')$, for $W(2,t)$, i.e., $A_2'$, equals $(2S_2' - 2S_6' + S_8')$, for $W(3,t)$, i.e., $A_3'$, equals $(2S_2' - 2S_4' + 2S_6' - S_8')$, for $W(4,t)$, i.e., $A_4'$, equals $(2S_1' - 2S_3' + 2S_5' - 2S_7' + S_8')$, for $W(5,t)$, i.e., $A_5'$, equals $(2S_1' - 2S_3' + 2S_4' - 2S_5' + 2S_7' + S_8')$, for $W(6,t)$, i.e., $A_6'$, equals $(2S_1' - 2S_2' + 2S_3' - 2S_5' + 2S_6' - 2S_7' + S_8')$, and for $W(7,t)$, i.e., $A_7'$, equals $(2S_1' - 2S_2' + 2S_3' - 2S_4' + 2S_5' - 2S_6' + 2S_7' - S_8')$.

The Walsh analyzer 196 of FIG. 16 produces signals proportional to Walsh coefficients by approximating the solution of the integral equation $A_i' = (-1/T)$ (Wa1' $(i,t)$)

$$\int_0^T f(t)dt.$$

Wherein $i \in \{0,1,2,3,...\}$, each $A_i'$ corresponds to a Walsh coefficient of the Walsh series expansion of the signal received by the sampler 190 (FIG. 15) and (Wa1' $(i,t)$) represents the derivatives of the Walsh basis functions $W(i,t)$. In solving this equation, the $$\int_0^T f(t)dt$$

is approximated by the samples provided by the sampler 190 (FIG. 15) and the normalizing factor 1/T is dropped. In matrix form this integral equation is thus reduced to [A] = [Wa1'][S], wherein [A] is a column matrix of the desired signals proportional to the Walsh coefficients, (i.e., $A_0'$ through $A_7'$), [S] is a column matrix of the stored samples from the sampler 190 (i.e. $S_1'$ through $S_8'$) and [Wa1'] is a square matrix related to the differentiated Walsh functions for producing signals corresponding to Walsh coefficients from samples. Therefore, the Walsh analyzer 196 comprises means for multiplying the matrix [Wal'] by the matrix [S] to produce its outputs.

The generation of the matrix [Wal'] related to the differentiated Walsh functions for converting group of eight samples into eight signals proportional to the Walsh coefficients will be described with reference to FIG. 17. The Walsh waves of FIG. 1 are illustrated in FIG. 17 over the interval of time from zero to T and are labeled A through H, with A corresponding to W(0,t), B corresponding to W(1,t), etc. Therefore, the rows A through H correspond to an array of Walsh functions ordered by sequency from W(0,t) through W(7,t). Eight equal sub-increments of time ending at times (T/8), (T/4), (3T/8), (T/2), (5T/8), (T/4), (7T/8) and T are formed over the interval from zero to T and result in columns A through H comprising the Walsh waves at the time each respective sub-increment ends. Thus, A is a column of the Walsh waves W(0,t) through W(7,t) at time T/8, B is a column of the Walsh waves at time T/4, etc.

The array of FIG. 17a is constructed from the similar rows and columns of the subdivided chart of Walsh functions of FIG. 17 and hence corresponding rows and columns of these figures are similarly labeled. The magnitude of the derivative of any Walsh wave of FIG. 1 with respect to time, at a particular time, is set equal to the magnitude of the shift in value of the wave at that time. Consequently, if, at a given time, the Walsh function has a constant value, then its derivative is zero. On the other hand, if the Walsh wave is changing from positive one to negative one, or vice versa, then the magnitude of the derivative is two. Finally, if the Walsh wave changes from either plus or minus one to zero, then the magnitude of the derivative is one. Furthermore, the derivative is defined to be positive if the change in the waveform occurring at the given time is in a positive direction (i.e. zero to (+1), or (−1) to (+1)) and negative if the change is in a negative direction (i.e. (+1) to zero, or (+1) to (−1)).

At the time represented by column A, namely time T/8 in FIG. 17, the waveform of row A is not changing to a new value. Therefore, the derivative of the waveform of row A at time T/8 is zero. Consequently, a zero is placed in row A, column A, of FIG. 17a. Similarly, zeros are placed in row A, columns B through G. At time T, the Walsh function of row A (FIG. 17), as well as the functions of rows B through H, are treated as if they return to zero. This is done to account for the dumping of the integrator circuit 260 of the sampler 190 (FIG. 15) which occurs at this time. Therefore, the waveform of row A (FIG. 17) is considered to drop from (+1) to zero at time T. Consequently, the derivative of the waveform at this time is (−1) and a (−1) is placed in row A, column H. Continuing this process for each row of Walsh functions of FIG. 17 results in the completed array of FIG. 17a.

The matrix [Wal'] of rank 8, shown in FIG. 17b is constructed from the array of FIG. 17a by assigning each element of the matrix the value found in the corresponding row and column of the array of FIG. 17a and then multiplying the entire matrix by the scalar (−1). The scalar multiplication eliminates the negative sign found on the right side of the integral equation. The analyzer of FIG. 16 multiplies the FIG. 17b matrix [Wal'] by the column of samples $S_1'$ through $S_8'$ to produce the signals $A_0'$ through $A_7'$. The matrix [Wal'] is related in the above manner to the differentiated Walsh functions for producing eight signals proportional to Walsh coefficients from the group of eight samples. In a similar manner the [Wal'] matrices of other ranks can be generated for applications wherein any lesser or greater number of signals proportional to Walsh function coefficient outputs are to be obtained from a lesser or greater number of samples.

Although the description found in the remainder of the specification applies when either the FIG. 13, or FIG. 16 form of Walsh analyzer is utilized, it proceeds under the assumption that the variety of FIG. 13 has been selected.

The outputs $A_0$ through $A_7$ from the Walsh analyzer 196 are slowly varying DC signals which are constant for a fixed set of test specimen parameters. As any test parameter changes, all these outputs will generally vary, but in slightly different degrees. This slowly varying DC signal occurs because when the probe 12 is moved relative to the specimen, for example through the tube 14 (FIG. 5), it passes in proximity to sections of the specimen containing variations in its characteristics (i.e. defects). These variations in turn affect the probe output signal and hence the outputs of the Walsh analyzer 196.

COMBINING NETWORK

The combining means or network 18 (FIG. 4) comprises means responsive to the Walsh coefficient outputs or series of Walsh function representations from the Walsh analyzer or expander 196 for producing an output indicating at least one of the variable characteristics of the sample. A plurality of the Walsh coefficient outputs or representations are fed to the combining network 18 for this purpose.

The combining network 18 may include a coefficient combining means or circuit 378 (FIG. 18) such as the illustrated array of transformation rotators 380 through 390. As explained below, the coefficient combining circuit 378 operates on the inputs thereto to produce at least one output representative of one of the variable characteristics of the sample 14. This latter output can be displayed on a suitable display device 392 (FIG. 4) such as a storage oscilloscope 394 (FIG. 18) or equivalent recorder.

For purposes of illustration, the coefficient combining circuit 378 will be described with respect to its operation on a plurality of inputs received directly from the Walsh analyzer 196, in particular with reference to the specific example of its operation on four Walsh coefficient outputs $A_1$, $A_2$, $A_3$ and $A_4$. It is to be understood that the coefficient combining circuit is not limited to operating on four such outputs, but can easily extended to receive additional outputs.

The coefficients $A_1$, $A_2$, $A_3$ and $A_4$ constitute four inputs to the coefficient combining circuit 378. In general, W is defined as the number of inputs to the coefficient combining circuit, in this case four. Each of the transformation rotators 380 through 390 is typically identical to the others and together they operate to combine the W inputs and produce at least one output therefrom.

The rotators 380 through 390 may be of the type shown in FIG. 19 wherein each rotator has two inputs 400 and 402. The input 400 is fed through serially connected inverters 404 and 406 to an input of a sine-cosine potentiometer 410. A portion of output from the inverter 404 is also fed to the other input of the potentiometer 410. Similarly, the input 402 is fed through serially connected inverters 412 and 414 to an input of a sine-cosine potentiometer 416. A portion of the output from the inverter 412 is fed to the other input of potentiometer 416. The sine-cosine potentiometers 410, 416 are mounted on a common shaft but with the rotational relationship of the potentiometers 410 and 416 being rotationally displaced ninety degrees with respect to each other. The sine-cosine function output signals from the potentiometer 410 are fed respectively to an input of summation operational amplifiers 418 and 420. The sine-cosine output signals from the potentiometer 416 are fed respectively to other inputs of amplifiers 418 and 420. The summation signals from amplifiers 418 and 420 are fed respectively to outputs 422 and 424.

For the transformation rotator of FIG. 19, with an input signal X supplied to the input 400 and an input signal Y supplied to the input 402, the inverters 404, 406, 412 and 414 operate to effect positive and negative polarity signal values of the respective input signals X and Y. Thus, the positive and negative polarities of the input signals $(X, -X$ and $Y, -Y)$ are applied across the respective potentiometers 410 and 416 to provide driving voltages therefor. With the connections as shown in FIG. 19, sine-cosine potentiometer 410 provides outputs $-X \sin \phi$ and $-X \cos \phi$ and sine-cosine potentiometer 416 provides outputs $Y \sin \phi$ and $-Y \cos \phi$. The summation operational amplifier 418 combines the sine-cosine outputs of potentiometers 410, 416 to provide an output, on output terminal 422, of $E_1 = X \cos \phi - Y \sin \phi$. Similarly, summation operation amplifier 420 sums the sine output from the potentiometer 410 and the cosine output from the potentiometer 416 to provide an output signal, on terminal 424, of $E_2 = X \sin \phi + Y \cos \phi$. In the equations for $E_1$ and $E_2$, X equals the input signal on terminal 400, Y equals the input signal on terminal 402, each $\phi$ equals the rotational angle of the common shaft of the potentiometers 410 and 416 from a reference angle.

The ninety degree rotational displacement between ganged potentiometers 410 and 416 may be eliminated by the addition of an inverter which receives the cosine output of the potentiometer 416 and feeds its output to an input of the summation operational amplifier 420.

Referring again to FIG. 18, the illustrated array of rotators is arranged in three columns or stages. The first stage receives as its inputs the signals $A_1, A_2, A_3$ and $A_4$, the second stage receives as its inputs certain of the outputs from the rotators of the first stage and the third stage receives as its input certain of the outputs from the rotators of the second stage. In general, there are W-1 interconnected columns or stages when this type of rotator arrangement is utilized, that is, one less stage than the number of inputs to the array of rotators. A stage is defined to include at least one rotator and the first stage receives, at its inputs, signals which have not been fed through rotators, the second stage receives input signals which have been fed through one stage of rotators, the third stage receives signals which have been fed through two successive stages of rotators, etc. In most cases the number of inputs to be combined are such that a plurality of rotators are included in the first stage and a plurality of stages are utilized. Thus, the stages may be sequentially numbered from one, corresponding to the stage receiving the inpus $A_1, A_2, A_3, A_4$ in FIG. 18, to W-1, corresponding to the stage which provides the input to the parameter display 392 or scope 394. If A is defined to equal the number of a particular stage, then there are typically W-A rotators in such stage. For example, considering the second stage of FIG. 18, A would equal two, W-A would equal four minus two, or two, and consequently there are two rotators present in this stage. Each of the rotators is connected to receive only one signal at each of its input terminals. Furthermore, only one of the outputs of each rotator is fed to a succeeding column of rotators except for the two outputs from the last stage which are both fed to the scope 394. When three or more (i.e., (W-1)≧2) inputs are being provided to the first stage of rotators, (W-2) of the W input signals are connected to the inputs of two separate rotators of the first column and the remaining two of the W input signals are connected to an input of separate single rotators of the first column. Therefore, in FIG. 18, $A_2$ is fed to one input of rotator 380 and also to one input of rotator 382, input $A_3$ is fed to one input of rotator 382 and also to one input of rotator 384, and inputs $A_1$ and $A_4$ are fed to one input of separate rotators 380 and 384, respectively. In addition, when ((W-1)≧2), and for columns or stages numbered 2 through W-2, if there are N outputs received from the preceding column, then N-2 of such outputs are connected to an input of two separate rotators in the succeeding column and the remaining two of the N outputs are each connected to an input of a separate rotator of the succeeding column. For example, an output of rotator 382 is connected to an input of rotator 386 and also to an input of rotator 388, while the outputs of rotators 380 and 384 are fed to rotators 386 and 388, respectively. The single rotator of the last stage (i.e., 390) receives at each input one of the outputs from each of the two rotators of the preceding column. Furthermore, in the event only two signals corresponding to Walsh coefficients are of interest (i.e., (W-1) = 1), then one of these coefficients will be fed to each input terminal of the only rotator.

FIG. 20 shows a two dimensional representation of signals which may be caused by the four input signals $A_1, A_2, A_3$ and $A_4$. The identified signals are P430, P432, P434 and P436. For purposes of illustration, the signal P430 may represent the parameter or variable characteristic of the sample which is to be retained and displayed. The other signals, P432, P434 and P436, then represent variables not of interest which are to be masked, or discriminated against, to enable a representation of signal P430 to be displayed on the scope 394. The transformation rotators 380, 382 and 384 are adjusted by rotation of their potentiometer shafts to give the plane projection shown in FIG. 20b, in which the effects of P432, P434 and P436 appear more collapsed. The transformation rotators 386 and 388 are then adjusted by rotation of their respective potentiometer shafts to give the plane projections shown in FIG. 20c wherein the signals P432, P434 and P436 appear still more collapsed. Further adjustments of these latter three transformation rotators results in a projection of the signals P432 through P436 as an edge view in FIG. 20d. Final adjustment of the rotator 390 causes the waveform of FIG. 20e to appear on the scope 394. It should be noted that even though these signals P430, P432, P434 and P436 are lissajou patterns of some complexity at the start, all of their final projections can be made to occur essentially in one straight line. In addition, the signal pattern caused by the variable parameter to be retained, (i.e., P430) has in general a component normal to the other three signals. Thus, the last rotation causes the undesired signals P432, P434 and P436 to give a deflection in only the horizontal direction while at the same time the signal of interest P430 has components in the vertical direction.

As a more specific example, the rotators 380, 382 and 384 of the first stage may be adjusted to eliminate the effects of probe wobble on the probe output signal. By probe wobble it is meant movements of the probe 12 (i.e., FIG. 5) which vary the distance between the coils 118, 126 (FIG. 4) and the sample 14. Such movements affect the eddy currents generated in the sample and hence the probe output. The rotators 386, 388 and 390 may then be adjusted to eliminate the effects caused by supporting structures, such as the effects of the metallic support 134 (FIG. 5), on the probe output signal. Therefore, an indication of the presence of a defect, such as notch 132, may be produced even though the notch 132 happens to be positioned in proximity to or underneath the support 134.

Although other arrays of rotators are suitable, an array of stages of rotators as described above results in an easily adjustable and reliable eddy current testing device. Adjustment of the rotators is facilitated because, unlike existing arrangements, it is not necessary to make the adjustment either in one step, or in a series of converging adjustments back and forth between all of the rotators. Instead, the rotators 380, 382 and 384 may first be adjusted to, for example, eliminate the effects of probe wobble. Thereafter, they may be left in their adjusted positions while the rotators 386, 388 and 390 are subsequently adjusted. Operation of the eddy current device of the present invention does not require relative movement between the probe 12 and the sample 14. However, if a stationary probe is used, then instead of a lissajou pattern, a spot would appear on the oscilloscope 394 (FIG. 18). The position of the spot on the oscilloscope screen would then provide an indication of the variable characteristic of interest.

An alternative combining network 18 is shown in FIG. 21. When this type of combining network is employed, the device is the same as previously described except that the filtering means may comprise a conventional low pass wave filter 444. When included, filter 444 may replace the sequency filter 150, or be connected between the sequency filter 150 and the sampler 190. In the event the low pass wave filter 444 is substituted for the sequency filter 150, then typical effects of a flaw (i.e., notch 132) on the signal present at the input F of the filter are shown in FIG. 22F and at the output G are shown in FIG. 22G. In addition to the coefficient combining circuit 378, the combining network 18 of FIG. 21 includes a Walsh to Fourier transforming means or transformation circuit 450. The Walsh to Fourier transformation circuit 450 converts the series of Walsh function representations provided by the Walsh analyzer 196 into a series of Fourier function representations of the signal received by the sampler 190. That is, the transformation circuit 450 converts the signals proportional to the Walsh coefficients from the Walsh analyzer 196 into a plurality of signals each proportional to a Fourier coefficient of the Fourier series expansion of the signal received by the signal sampler 190. A plurality of these signals proportional to the Fourier coefficient are then fed to the coefficient combining means or circuits 378, which in this application may be considered a means for combining the series of Fourier function representations, wherein they are combined as previously described for the signals proportional to Walsh coefficients. The W inputs to the coefficient combining circuit therefore correspond to the output of the Walsh analyzer 196 in that they are either signals proportional to the Walsh coefficients received directly from analyzer 196 or signals proportional to Fourier coefficients generated by the transformation circuit 450 from the outputs of the analyzer 196.

Figure 23:
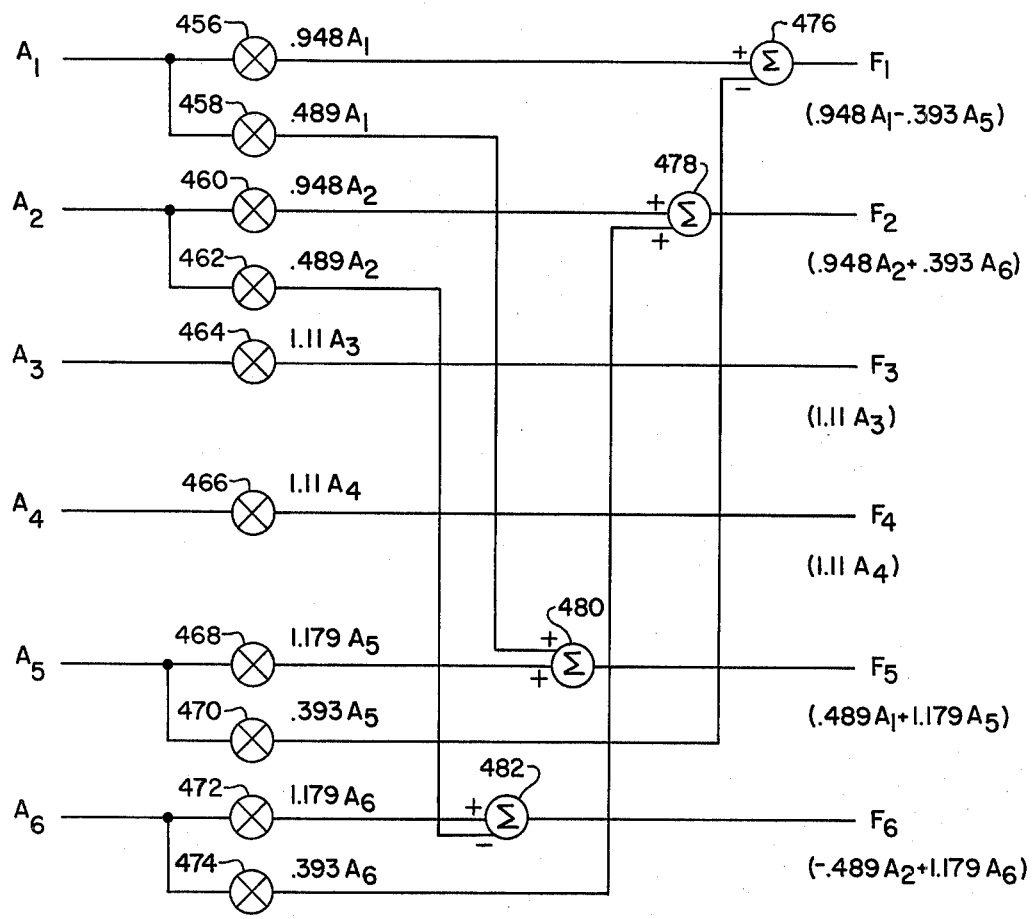
FIG. 23 illustrates in more detail a form of Walsh to Fourier transformation circuit portion of the device of FIG. 21.

A Walsh to Fourier transformation circuit 450 suitable for converting six outputs from the Walsh analyzer 196, namely $A_1$ through $A_6$, into corresponding Fourier function components $F_1$ through $F_6$ is illustrated in FIG. 23. A first group of multipliers 456 through 474 receive signals from the Walsh analyzer 196 and multiply them to provide outputs therefrom of $0.948A_1$, $0.489A_1$, $0.948A_2$, $0.489A_2$, $1.11A_3$, $1.11A_4$, $1.179A_5$, $0.393A_5$, $1.179A_6$, and $0.393A_6$, respectively. Certain of these partial results are fed into summation circuits 476, 478, 480 and 482 which are each capable of performing addition and subtraction. The outputs from the summation circuits, together with the outputs from the multipliers 464 and 466, constitute the outputs $F_1$ through $F_6$, wherein $F_1$ equals $(0.948A_1 - 0.393A_5)$, $F_2$ equals $(0.948A_2 + 0.393A_6)$, $F_3$ equals $(1.11A_3)$, $F_4$ equals $(1.11A_4)$, $F_5$ equals $(0.489A_1 + 1.179A_5)$ and $F_6$ equals $(-0.489A_2 + 1.179A_6)$. A plurality of these outputs are then coupled to an appropriate coefficient combining circuit 378.

In general, the Fourier coefficients are related to the Walsh coefficients by a matrix equation $[W] = [B][F]$. In this equation, $[W]$ is a column matrix of Walsh coefficients of a Walsh series expansion of a signal, $[F]$ is a column matrix of the desired Fourier coefficients of a Fourier series expansion of the signal, and the matrix $[B]$ corresponds to an infinite Hilbert matrix a portion of which is shown in Table I. The rows $j$ of this Hilbert matrix can be numbered, from top to bottom, 0,1,2, ... , and the columns $k$ can be numbered, from left to right, 0,1,2, ....

TABLE I $$\begin{bmatrix}
1 & 0 & 0 & 0 & 0 & 0 & 0 & 0 & 0 & 0 & 0 & 0 & 0 & 0 & 0 & 0 & 0 & \cdots \\
0 & 0.900 & 0 & 0 & 0 & 0.300 & 0 & 0 & 0 & 0.180 & 0 & 0 & 0 & 0.129 & 0 & 0 & 0 & \cdots \\
0 & 0 & 0.900 & 0 & 0 & 0 & -0.300 & 0 & 0 & 0 & 0.180 & 0 & 0 & 0 & -0.129 & 0 & 0 & \cdots \\
0 & 0 & 0 & 0.900 & 0 & 0 & 0 & 0 & 0 & 0 & 0 & 0.300 & 0 & 0 & 0 & 0 & 0 & \cdots \\
0 & 0 & 0 & 0 & 0.900 & 0 & 0 & 0 & 0 & 0 & 0 & 0 & -0.300 & 0 & 0 & 0 & 0 & \cdots \\
0 & -0.373 & 0 & 0 & 0 & 0.724 & 0 & 0 & 0 & 0.435 & 0 & 0 & 0 & -0.053 & 0 & 0 & 0 & \cdots \\
0 & 0 & 0.373 & 0 & 0 & 0 & 0.724 & 0 & 0 & 0 & -0.435 & 0 & 0 & 0 & -0.053 & 0 & 0 & \cdots \\
0 & 0 & 0 & 0 & 0 & 0 & 0 & 0.900 & 0 & 0 & 0 & 0 & 0 & 0 & 0 & 0 & 0 & \cdots \\
0 & 0 & 0 & 0 & 0 & 0 & 0 & 0 & 0.900 & 0 & 0 & 0 & 0 & 0 & 0 & 0 & 0 & \cdots \\
0 & -0.074 & 0 & 0 & 0 & -0.484 & 0 & 0 & 0 & 0.650 & 0 & 0 & 0 & 0.268 & 0 & 0 & 0 & \cdots \\
0 & 0 & -0.074 & 0 & 0 & 0 & 0.484 & 0 & 0 & 0 & 0.650 & 0 & 0 & 0 & -0.268 & 0 & 0 & \cdots \\
0 & 0 & 0 & -0.373 & 0 & 0 & 0 & 0 & 0 & 0 & 0 & 0.724 & 0 & 0 & 0 & 0 & 0 & \cdots \\
0 & 0 & 0 & 0 & 0.373 & 0 & 0 & 0 & 0 & 0 & 0 & 0 & 0.724 & 0 & 0 & 0 & 0 & \cdots \\
\vdots & \vdots & \vdots & \vdots & \vdots & \vdots & \vdots & \vdots & \vdots & \vdots & \vdots & \vdots & \vdots & \vdots & \vdots & \vdots & \vdots &
\end{bmatrix}$$

This particular Hilbert matrix is described by Blackman in an article entitled "Sinusoids versus Walsh Functions", in the Proceedings of the IEEE, Volume 16 No. 3, March 1974.

The above matrix equation can be adapted for use in converting a given finite number of outputs from the Walsh analyzer 196 into a corresponding finite number of signals proportional to Fourier coefficients. This is explained below in connection with the conversion of the signals $A_1$ through $A_6$ into the corresponding signals $F_1$ through $F_6$.

Initially, a square matrix [B'], shown in Table II for this case, is extracted from the general matrix of Table I.

TABLE II $$\begin{bmatrix} 0.900 & 0 & 0 & 0 & 0.300 & 0 \\ 0 & 0.900 & 0 & 0 & 0 & -0.300 \\ 0 & 0 & 0.900 & 0 & 0 & 0 \\ 0 & 0 & 0 & 0.900 & 0 & 0 \\ -0.373 & 0 & 0 & 0 & 0.724 & 0 \\ 0 & 0.373 & 0 & 0 & 0 & 0.724 \end{bmatrix}$$

The rank of the extracted matrix is equal to the number of signals from the Walsh analyzer 196 which are to be transformed into signals corresponding to Fourier coefficients. Since it is desired to obtain the signals $F_1$ through $F_6$, the rows of [B], wherein $j\epsilon\{1,2,\ldots 6\}$, are selected and since the signals $A_1$ through $A_6$ are to be converted, the columns of [B], wherein $k\epsilon\{1,2,\ldots 6\}$, are selected. The elements of [B] found at the intersection of the selected rows and columns, that is the elements $A_{jk}$ of [B], then form the matrix of Table II. Similarly, if the conversion of the signals $A_2$ through $A_5$ into the signals $F_2$ through $F_5$ is desired, the rows $j\epsilon\{2,3,4,5\}$ and columns $k\epsilon\{2,3,4,5\}$ are selected from [B] and used to construct another [B'] matrix.

The infinite equation [W] = [B][F] can be rewritten in the form [A] = [B'][F] for use in converting a given finite number of signals corresponding to Walsh coefficients into a given finite number of signals corresponding to Fourier coefficients. In this latter equation, [A] is a column matrix of the Walsh analyzer 196 outputs to be converted, [F] is a column matrix of the desired Fourier function component signals and [B'] is the corresponding matrix obtained from the Table I matrix. Multiplying [B'] by [F] results in the following set of six equations in the example under consideration.

(1) $A_1 = 0.9 F_1 + 0.3 F_5$
(2) $A_2 = 0.9 F_2 - 0.3 F_6$
(3) $A_3 = 0.9 F_3$
(4) $A_4 = 0.9 F_4$
(5) $A_5 = -0.373 F_1 + 0.724 F_5$
(6) $A_6 = 0.373 F_2 + 0.724 F_6$

Simultaneous solution of these equations results in the following set of equations:

(1) $F_1 = 0.948 A_1 - 0.393 A_5$
(2) $F_2 = 0.948 A_2 + 0.393 A_6$
(3) $F_3 = 1.11 A_3$
(4) $F_4 = 1.11 A_4$
(5) $F_5 = 0.489 A_1 + 1.179 A_5$
(6) $F_6 = -0.489 A_2 + 1.179 A_6$

The Walsh to Fourier transformation circuit of FIG. 23 is wired to combine the outputs $A_1$ through $A_6$ from the Walsh analyzer 196 in accordance with the latter set of equations to produce the Fourier function representations $F_1$ through $F_6$. In an identical manner the transformation circuit of FIG. 23 may be designed to convert any number of Walsh analyzer outputs into corresponding Fourier coefficient outputs.

The low pass filter 444 (FIG. 21) eliminates the higher frequency components of the signal it receives so that a more exact conversion from a finite set of signals proportional to Walsh coefficients to a corresponding set of signals proportional to Fourier coefficients can be made. Under certain circumstances, for a more precise determination of the Fourier coefficients of a signal from its first M Walsh coefficients it is desirable that the signal be bandlimited to have M or fewer harmonics. For example, when the output of the bridge drive 40 contains more than M harmonics, the use of a low pass filter 444 allows the Fourier coefficients to be more exactly obtained. In addition, a low pass filter may be used to reduce the undesired effects of high frequency noise.

Figure 24:
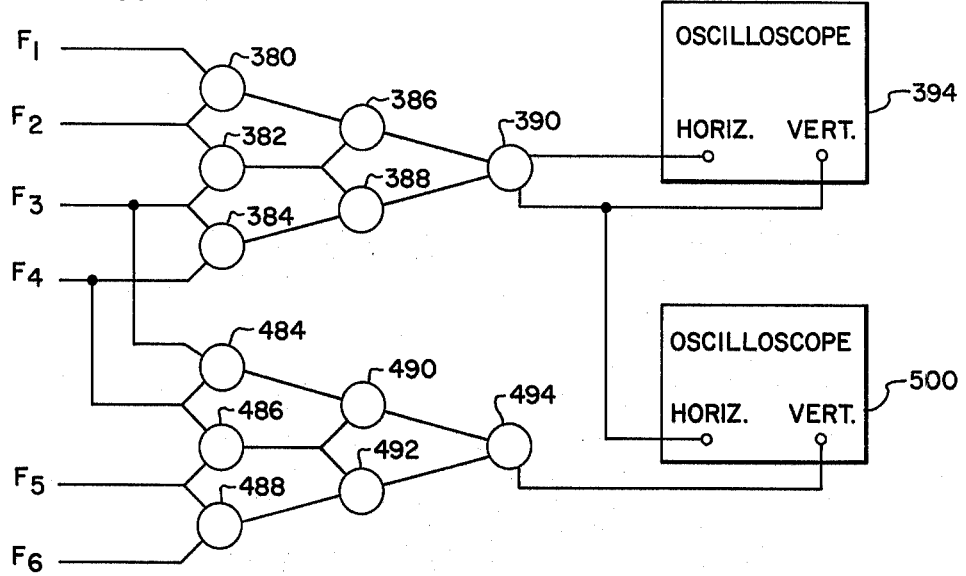
FIG. 24 is a block diagram of another suitable form of coefficient combining network.

A plurality of the signals $F_1$ through $F_6$ are fed to a coefficient combining circuit 378. The combining circuit 378 may be similar to that shown in FIG. 18, or alternatively, of the type shown in FIG. 24. This latter type differs from that shown in FIG. 18 in that it includes a second array of three columns of rotators 484 through 494 and a second oscilloscope 500. The signals $F_1$, $F_2$, $F_3$ and $F_4$ are fed into and combined by the first array of rotators, in the manner described in connection with FIG. 18, to produce the output at the scope 400 of the form shown in FIG. 20e. Assuming that an excitation signal comprised of more than two frequencies components is being utilized (for example, the summing amplifier 94 of FIG. 8 sums sinusoid signals of 100 KH, 200 KH and 300 KH from sinusoidal function generators 80, 82 and 84), then the signals $F_5$ and $F_6$ contain additional usable information about the test sample. Returning to FIG. 24, the signal $F_3$ is fed into one input of rotator 484 and the signal $F_4$ to the other input. The rotator 486 receives as one input the the signal $F_4$ and the signal $F_5$ is fed to its other input and also to one input of the rotator 488. In addition, the signal $F_6$ is fed to the other input of the rotator 488. The second array of rotators 484 through 494 are adjusted in the same manner as the first array of rotators. However, once they have been adjusted, they produce an output such as P430' (FIG. 20f) which is somewhat different in appearance from the output P430 (FIG. 20e) produced by the rotator 390. This difference occurs because the signals $A_1$ through $A_6$ and corresponding signals $F_1$ through $F_6$ progressively contain more higher frequency eddy current information when moving from signals having lower numbered subscripts to subscripts having higher numbers. When a portion of the vertical input to the scope 394 is fed to the horizontal input of the scope 500 and the vertical component of the signal from the rotator 494 is fed to the vertical input of the scope 500, a pattern is produced on scope 500 which has an angle or phase difference. In some applications, the phase difference may be utilized to give an indication of the dimension (i.e., depth) of a flaw. The behavior of eddy currents are such that the use of lower frequency excitation signals cause eddy currents which fall off less rapidly with the depth of penetration into the sample than caused by higher frequency excitation signals. Consequently, in some cases, when the signals containing higher frequency eddy current information, as in the case of the vertical component of the output from the rotator 494, are compared with the signals containing lower frequency eddy current information, such as the vertical component of the output from the rotator 390, the differences (i.e., phase difference) enables the dimensions of the flaw to be more fully determined.

OPERATION

With reference to FIGS. 4 and 5, the excitation signal generator 10 generates and applies an excitation signal to the bridge circuit 110 and hence to the coils 118 and 126. When the probe 12 is in proximity to the sample 14 (i.e., FIG. 5), the excitation signal causes the generation of eddy currents in the sample. The eddy currents vary depending on the variable characteristics of the sample 14 and hence will change when the coils 118, 126 are moved to a position in proximity to the notch or flaw 132. The coils 118, 126 in turn sense the eddy currents to produce an output in accordance with their nature.

The probe output signal is fed through the transformer 140, amplified by the amplifier 142 and has its waveform altered to a squared up version by the sequency filter 150. The output from the sequency filter 150, which corresponds to at least a portion of the probe output, is sampled by the signal sampler 190 to produce a plurality of stored signal samples. The Walsh analyzer 196 converts the samples into a plurality of signals each corresponding to a Walsh coefficient of the Walsh series expansion of the probe output signal. Since these letter signals are derived from the probe output signal, they also vary with the nature of the eddy currents generated in the sample 14 and therefore with the variable characteristic of the sample.

The combining network 18 receives and combines a plurality of the signals produced by the Walsh analyzer 196 to provide at least one output indicating one of the variable characteristics of the sample 14. That is, the network 18 minimizes the effects of certain variable characteristics on its output, for example those caused by eddy currents flowing in the support 134 (FIG. 5) so that its output represents at least one selected variable characteristic of interest, such as the presence of the flaw 132. The parameter display 392 may receive the output from the combining network 18 to provide a visual representation thereof.

It will be appreciated that any or all of the various functions performed by the Walsh analyzer, multipliers, integrating devices, summing circuits and other circuitry as hereinbefore described can be likewise implemented employing general or special purpose digital computers or computer elements. The programming of general and special computer apparatus to carry out the various functions of addition, subtraction, multiplication, etc., as described above, is straightforward. In such cases, the computer elements perform in essentially the same manner, or in an equivalent manner, to circuitry hereinbefore disclosed.

Having illustrated and described our invention with reference to preferred embodiments, it should be apparent to those persons skilled in the art that such invention may be modified in arrangement and detail without departing from the principals thereof.

We claim:

1. An eddy current testing apparatus for measuring one or more variable characteristics of an electrically conductive sample comprising:
   test coil means;
   means for generating an excitation signal equivalent to a summation of finite number of Walsh functions and for applying said excitation signal to said test coil means while said test coil means is in proximity to said sample to provide an output from said test coil means which varies with variations in the characteristics of the sample;
   expander means for producing a representation of said output from said test coil means as a plurality of signals each proportional to a coefficient of a squarewave expansion of said signal;
   and means responsive to said plurality of signals for producing an output indicating at least one of the variable characteristics of the sample.

2. The apparatus according to claim 1 wherein said output from said test coil means comprises a generated waveform and wherein said expander means includes means for sampling said generated waveform and for converting said samples to values, and means for combining said values to produce said representation of said generated signal.

3. An eddy current testing apparatus for measuring one or more variable characteristics of an electrically conductive test sample comprising:
   means for generating a signal which varies in accordance with the characteristics of the sample;
   Walsh expander means for receiving at least a portion of said generated signal and for spectrally decomposing said received signal into a series expansion of Walsh function representations;
   and means responsive to said series of Walsh function representations for producing an output indicating at least one of the variable characteristics of the sample.

4. The device according to claim 3 wherein said Walsh expander means includes means for sampling said received signal and means for combining said samples to transform the same into said Walsh function representations.

5. The device according to claim 3 wherein said means responsive to said series of Walsh function representations includes Fourier transforming means for converting said series of Walsh function representations into a series of Fourier function representations of said received signal and means for combining said series of Fourier function representations to provide said output indicating at least one of the variable characteristics of the sample.

6. An eddy current testing apparatus for measuring at least one variable characteristic of an electrically conductive test sample comprising:
   test coil means;
   means for generating and applying an excitation signal to said test coil means while said test coil means is in proximity to said sample to provide an output from said test coil means which varies in accordance with the characteristics of said sample;
   analyzer means coupled to said test coil means for expanding a received signal corresponding to at least a portion of said test coil means output into a plurality of signals each proportional to a Walsh coefficient of the Walsh series expansion of said received signal;
   and combining means for combining a plurality of said signals each proportional to a Walsh coefficient to give at least one output indicating one of the variable characteristics of the sample.

7. The eddy current testing apparatus of claim 6 wherein said analyzer means includes sampling means for sampling said received signal and means for combining the samples into said signals each proportional to a Walsh coefficient.

8. The eddy current testing apparatus of claim 7 wherein said means for generating and applying an excitation signal to said test coil means includes sinusoidal signal generator means for producing a multifrequency sinusoidal excitation signal and synchronizing means for synchronizing said sampling means to said excitation signal.

9. The eddy current testing apparatus of claim 7 wherein said means for generating and applying an excitation signal to said test coil means includes means for generating a multifrequency sinusoidal excitation signal comprising square wave generator means for producing an output of square wave pulses, first binary counter means driven by said square wave generator means for producing at least one binary output, a plurality of phase lock loop sine wave function generator means each receiving an output of said first binary counter means, wherein one of said function generators produces a sine wave output of a first predetermined frequency and another produces a sine wave output of a second predetermined frequency, and means for summing outputs of said function generator means to provide said multifrequency sinusoidal excitation signal;

said apparatus also including second binary counter means for receiving an output from said first binary counter means and for producing an encoded binary output, decoder means connected to said second binary counter means for receiving said encoded binary output, said decoder means also being coupled to said sampling means for providing a plurality of sampling pulses to said sampling means, and wherein said sampling means produces said samples in response to said sampling pulses.

10. The eddy current testing apparatus of claim 7 wherein said combining means includes Fourier transforming means for converting said signals proportional to the Walsh coefficients into a plurality of signals each proportional to a Fourier coefficient of the Fourier series expansion of said received signal and coefficient combining means for combining a plurality of said signals each proportional to a Fourier coefficient to provide said output indicating at least one of the variable characteristics of the test sample.

11. The eddy current testing apparatus of claim 7 wherein said means for generating and applying an excitation signal to said test coil means applies a periodic excitation signal to said test coil means, wherein said sampling means includes sample and average circuit means for periodically sampling said received signal over consecutive periods of time during each period of said periodic excitation signal and for separately storing said samples of said received signal so that said stored samples may be combined into said signals each proportional to a Walsh coefficient.

12. The eddy current testing apparatus of claim 11 wherein said means for combining said samples into said signals proportional to the Walsh coefficients comprises means for multiplying a matrix [H] and a column matrix [S] for the solution of the equation [A] = [H] [S], wherein [A] is a column matrix of the desired signals proportional to the Walsh coefficients, [H] is a Hadamard matrix related to the Walsh functions for producing Walsh coefficients from samples and [S] is a matrix of the stored samples.

13. The eddy current testing apparatus of claim 7 wherein said means for generating and applying an excitation signal to said test coil means applies a periodic excitation signal to said test coil means, wherein said sampling means includes integrator means for integrating said received signal over each period of said periodic excitation signal and for dumping said integrated signal at the end of each such period, and wherein said sampling means also includes sample and average circuit means for periodically sampling said integrated received signal during each period of said periodic excitation signal and for separately storing said samples of said integrated received signals so that said stored samples may be combined into said signals each proportional to a Walsh coefficient.

14. The eddy current testing apparatus of claim 13 wherein said means for combining said samples into said signals proportional to the Walsh coefficients comprises means for multiplying a matrix [Wal'] and a column matrix [S] for the solution of the equation [A] = [Wal'] [S], wherein [A] is a column matrix of the desired signals proportional to the Walsh coefficients, [S] is a matrix of the stored samples and [Wal'] is a matrix related to the differentiated Walsh functions for producing Walsh coefficients from said samples.

15. An eddy current testing apparatus for measuring at least one variable characteristic of an electrically conductive test sample comprising:
test coil means;
means for generating and applying an excitation signal to said test coil means while said test coil means is in proximity to said sample to provide an output from said test coil means which varies in accordance with the characteristics of said sample;
filtering means coupled to said test coil means for filtering a signal corresponding to the output signal of said test coil means;
sampling means connected to said filtering means for producing samples corresponding to the output of said filtering means;
Walsh analyzer means for combining said samples to provide a plurality of signals each proportional to a Walsh coefficient of the Walsh series expansion of the output of said filtering means;
and combining means for combining a plurality of said signals to give at least one output indicting one of the variable characteristics of the sample.

16. The eddy current testing apparatus of claim 15 wherein said means for generating and applying an excitation signal comprises means for generating and applying an excitation signal equivalent to a summation of a finite number of Walsh functions.

17. The eddy current testing apparatus of claim 15 wherein said means for generating and applying an excitation signal includes square wave generator means for producing an output of square wave pulses, binary counter means driven by said square wave generator means for producing an encoded binary output, decoder means connected to said binary counter means and coupled to said test coil means for decoding said encoded binary output to provide a periodic square wave excitation signal to said test coil means, said decoder means also being coupled to said sampling means for providing a plurality of sampling pulses to said sampling means, wherein said sampling means produces said samples in response to said sampling pulses.

18. The eddy current testing apparatus of claim 17 wherein said binary counter means includes a first binary counter for receiving the output of said square wave generator means and for producing a plurality of outputs and a second binary counter for selective connection to one of the outputs of said first binary counter to produce said encoded binary output.

19. The eddy current testing apparatus of claim 15 wherein said filtering means comprises sequency filter means, and wherein said combining means comprises coefficient combining means for directly receiving a plurality of said signals from said Walsh analyzer means and for combining such received signals to give said at least one output indicating one of the variable characteristics of the sample.

20. The eddy current testing apparatus of claim 15 wherein said filtering means comprises low-pass wave filter means, said combining means includes Fourier transforming means for converting said signals each proportional to a Walsh coefficient of the Walsh series expansion of the output of said filtering means into a plurality of signals each proportional to a Fourier coefficient of the Fourier series expansion of the output of said filtering means;

and wherein said combining means also includes coefficient combining means for receiving a plurality of said signals each proportional to a Fourier coefficient from said Fourier transforming means and for combining such received signals to give said at least one output indicating one of the variable characteristics of the sample.

21. The eddy current testing apparatus of claim 15 wherein said combining means includes coefficient combining means for receiving W input signals corresponding to said signals provided by said Walsh analyzer means, where W is at least two and not greater than the number of signals provided by said Walsh analyzer means, said coefficient combining means comprising W-1 columns of like transformation rotators, each transformation rotator including a pair of inputs and means for generating a first output $E_1 = X\cos\phi - Y\sin\phi$ and a second output $E_2 = X\sin\phi + Y\cos\phi$, where $X =$ an input signal applied to one of said rotator inputs, $Y =$ an input signal applied to the other of said rotator inputs and $\phi =$ a variable reference angle, each successive column comprising W-A of said transformation rotators, where A is the integral column number varying in sequence from one to W-1, the rotators of column number one being connected to receive said W input signals and each input of the rotators of each succeeding column being connected to receive only one of the output signals from the preceding column, and only one of the pair of outputs of each transformation rotator is fed to the succeeding column of rotators, and for W-1 at least equal to two there being W-2 of said W input signals connected to an input of two separate transformation rotators of the first column and the remaining two of said W input signals each being connected to an input of separate single transformation rotators of said first column, and for W-1 at least equal to two and column numbers two through W-2 there being N-2 of the N outputs received from each preceding column connected to an input of two separate transformation rotators of the succeeding column and the remaining two outputs received from each preceding column each being connected to an input of a separate transformation rotator of the succeeding column and wherein the single rotator of column number W-1 receives at each input a separate one of the outputs of the preceding column, and for W-1 equal to 1 the single rotator receives at each input a separate one of the W outputs, and means for displaying the first and second outputs $E_1$ and $E_2$ of column number W-1 to provide a display of a variable characteristic of said sample.

22. A method of eddy current testing an electrically conductive test sample comprising:
generating an excitation signal equivalent to a summation of a finite number of Walsh functions;
applying the excitation signal to a test coil means to generate eddy currents in the sample;
sensing a signal produced by the eddy currents in the sample;
producing a representation of a signal corresponding to at least a portion of the sensed signal as a series expansion of squarewave components;
combining said squarewave components to provide an output indicating at least one of the variable characteristics of the sample.

23. A method of eddy current testing an electrically conductive test sample comprising:
generating eddy currents in the sample;
sensing a first signal produced by the eddy currents in the sample;
expanding a second signal corresponding to at least a portion of the first signal into a plurality of signals each proportional to a Walsh coefficient of the Walsh series expansion of said second signal;
combining a plurality of said signals each proportional to a Walsh coefficient to give at least one output indicating one of the variable characteristics of the sample.

24. The method of claim 23 wherein said step of expanding a second signal comprises:
sampling said second signal to produce a plurality of samples;
combining the samples into the signals each proportional to a Walsh coefficient.

25. The method of claim 23 wherein said step of combining a plurality of said signals each proportional to a Walsh coefficient comprises:
converting said signals each proportional to a Walsh coefficient into a plurality of signals each proportional to a Fourier coefficient of the Fourier series expansion of said second signal;
and combining a plurality of said signals each proportional to a Fourier coefficient to give said at least one output indicating one of the variable characteristics of the sample.

26. A method of eddy current testing an electrically conductive test sample comprising:
generating an excitation signal;
applying said excitation signal to a test coil while the test coil is in proximity to said sample to provide an output from the test coil which varies in accordance with the characteristics of the sample;
filtering a signal corresponding to the output of the test coil to produce a filtered output signal;
sampling the filtered output signal to provide samples corresponding to the filtered output signal;
combining the samples to produce a plurality of signals each proportional to a Walsh coefficient of the Walsh series expansion of the filtered output signal;
and combining a plurality of said signals each proportional to a Walsh coefficient to give at least one output indicating one of the variable characteristics of the sample.

* * * * *